(12) United States Patent
Doherty et al.

(10) Patent No.: US 8,770,190 B2
(45) Date of Patent: Jul. 8, 2014

(54) CONNECTORS FOR CONNECTING COMPONENTS OF A BREATHING APPARATUS

(75) Inventors: Renee Frances Doherty, Coogee (AU); Chun Yui Lau, Sydney (AU); Philip Rodney Kwok, Chatswood (AU); Christopher John Baxter, Chatswood (AU); Angelene Marie Ozolins, Wahroonga (AU); Paul Anthony Green, Lindfield (AU)

(73) Assignee: ResMed Limited, Bella Vista (AU)

( * ) Notice: Subject to any disclaimer, the term of this patent is extended or adjusted under 35 U.S.C. 154(b) by 1597 days.

(21) Appl. No.: 12/108,764

(22) Filed: Apr. 24, 2008

(65) Prior Publication Data

US 2008/0264413 A1    Oct. 30, 2008

Related U.S. Application Data

(60) Provisional application No. 60/907,971, filed on Apr. 25, 2007, provisional application No. 60/980,208, filed on Oct. 16, 2007.

(51) Int. Cl.
- *A61M 16/08* (2006.01)
- *A61M 39/10* (2006.01)
- *A62B 9/04* (2006.01)

(52) U.S. Cl.
CPC ....... *A61M 16/0875* (2013.01); *A61M 16/0816* (2013.01); *A61M 39/1011* (2013.01); *A62B 9/04* (2013.01)
USPC ............. 128/202.27; 128/200.24; 128/205.23

(58) Field of Classification Search
USPC ........ 128/200.24, 202.27, 912; 285/184, 261, 285/146.1, 420, 930, 311, 312, 314, 320, 285/326, 358, 394, 87, 309, 148.27; 292/241, 240; 384/447; 16/438, 439; 138/120; 403/341, 252, DIG. 4; 604/250

See application file for complete search history.

(56) References Cited

U.S. PATENT DOCUMENTS

| | | | | |
|---|---|---|---|---|
| 3,761,117 A | * | 9/1973 | Shendure | 285/277 |
| 4,682,798 A | * | 7/1987 | Sauer | 285/148.13 |
| 4,775,173 A | * | 10/1988 | Sauer | 285/148.14 |
| 4,846,167 A | * | 7/1989 | Tibbals | 128/202.27 |
| 4,997,217 A | | 3/1991 | Kunze | |
| 5,123,677 A | * | 6/1992 | Kreczko et al. | 285/24 |
| 5,255,714 A | * | 10/1993 | Mullins | 137/614.04 |
| 5,267,757 A | * | 12/1993 | Dal Palu | 285/148.21 |
| 5,330,235 A | * | 7/1994 | Wagner et al. | 285/81 |

(Continued)

FOREIGN PATENT DOCUMENTS

| | | |
|---|---|---|
| WO | WO 2006/125252 A1 | 11/2006 |
| WO | WO 2007/143655 A2 | 12/2007 |
| WO | WO 2008/036625 A2 | 3/2008 |

*Primary Examiner* — Annette Dixon
(74) *Attorney, Agent, or Firm* — Nixon & Vanderhye P.C.

(57) ABSTRACT

A breathing apparatus includes components, including, but not limited to, a flow generator, a patient interface, and a delivery conduit. A connector for connecting components of the breathing apparatus includes a male connector, including a recess, extending from a first component, and a female connector, including a lever pivotally connected thereto, extending from a second component. A switch indicates a connection state of the connector. The switch includes a ring provided in an end of the first or second component and the ring includes a projection extending through an aperture in the end of the first or second component. The projection is movable between a first position and a second position to indicate the state of the connector.

56 Claims, 32 Drawing Sheets

(56) References Cited

U.S. PATENT DOCUMENTS

| | | | |
|---|---|---|---|
| 5,645,054 A * | 7/1997 | Cotner et al. | 128/204.23 |
| 5,921,239 A | 7/1999 | McCall et al. | |
| 6,279,573 B1 | 8/2001 | Johnson et al. | |
| 6,343,603 B1 | 2/2002 | Tuck et al. | |
| 6,832,610 B2 * | 12/2004 | Gradon et al. | 128/206.27 |
| 6,851,724 B2 | 2/2005 | Pittman, II | |
| 6,953,354 B2 | 10/2005 | Edirisuriya et al. | |
| 2002/0153012 A1 | 10/2002 | Gunaratnam et al. | |
| 2003/0151252 A1 * | 8/2003 | Dole | 285/312 |
| 2005/0077726 A1 | 4/2005 | White et al. | |
| 2005/0150497 A1 | 7/2005 | Eifler et al. | |
| 2005/0177994 A1 | 8/2005 | Ingram | |

\* cited by examiner

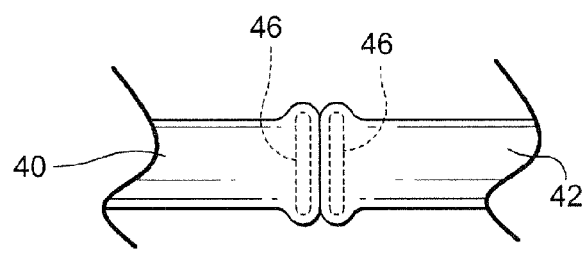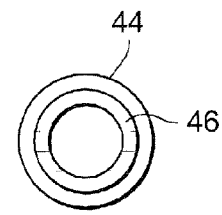
Fig. 2a        Fig. 2b
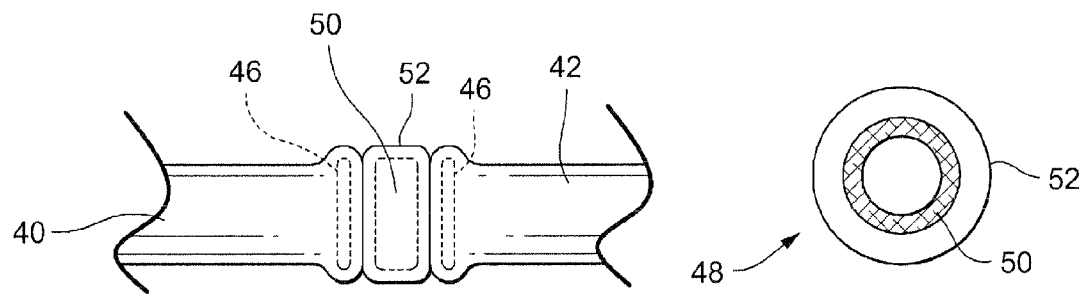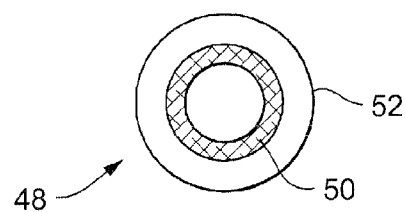
Fig. 3a        Fig. 3b
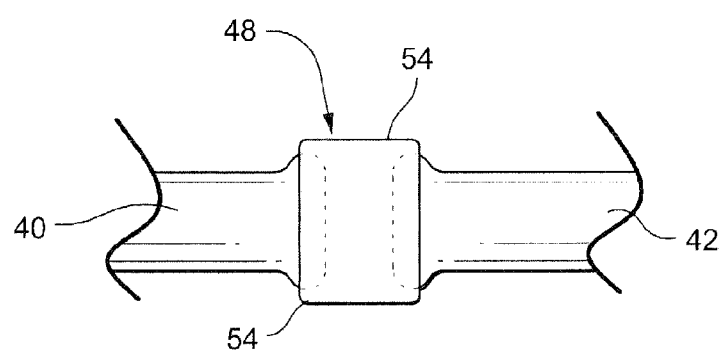
Fig. 4

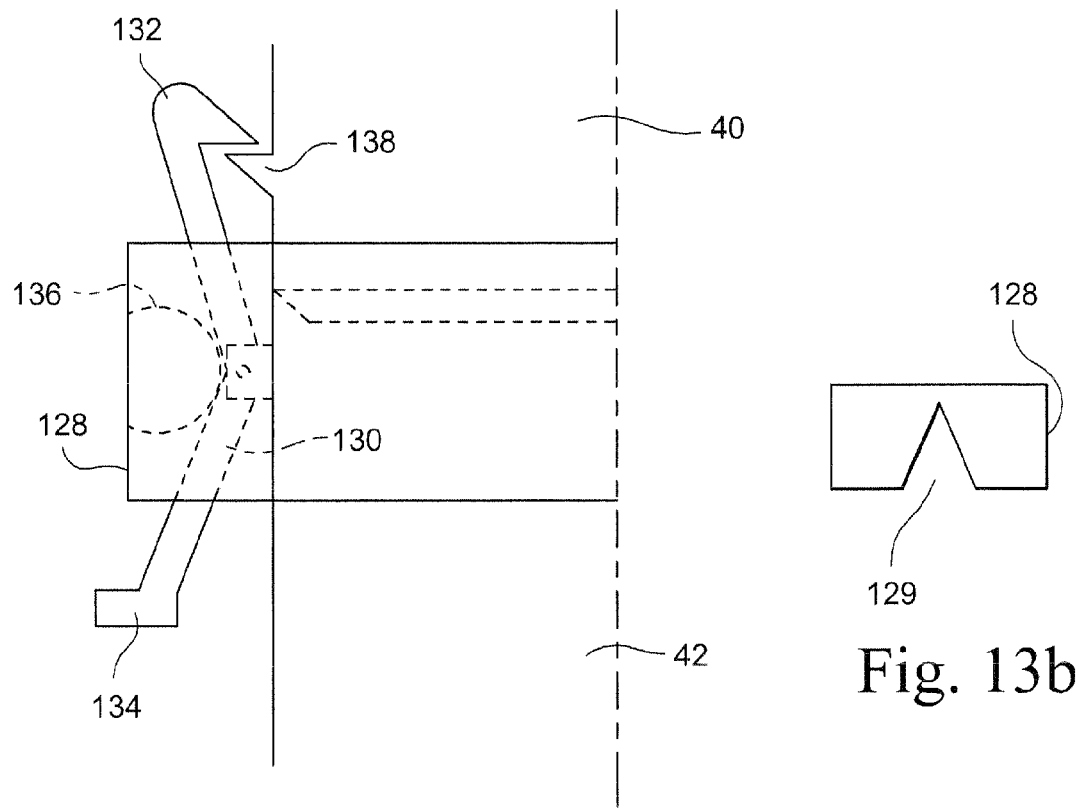
Fig. 13a
Fig. 13b
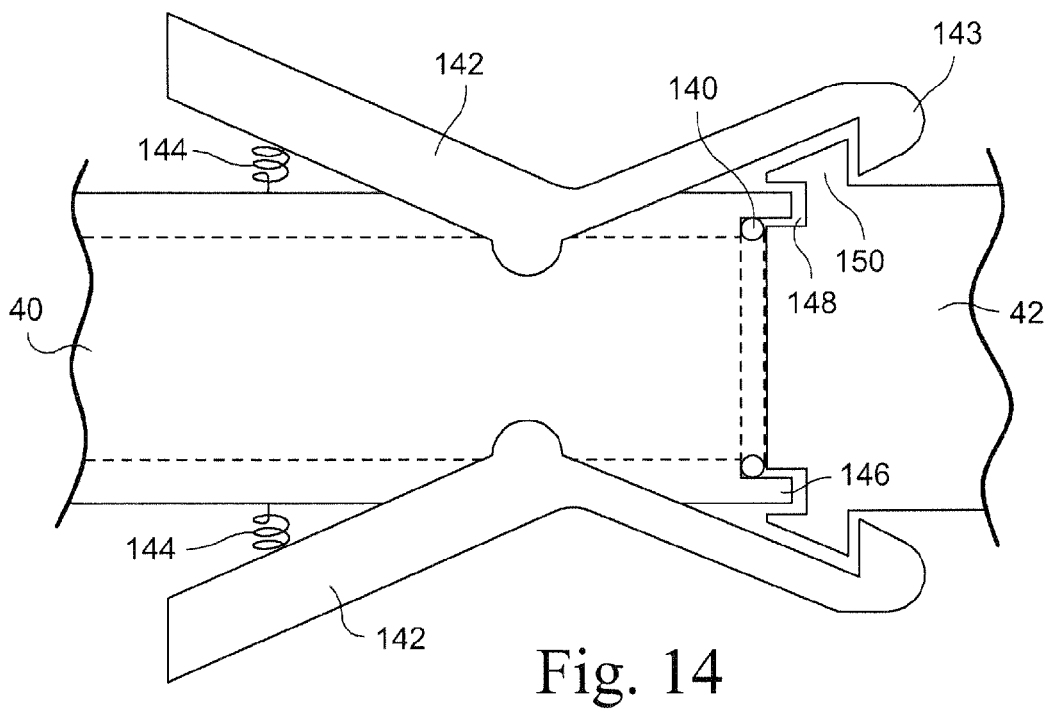
Fig. 14

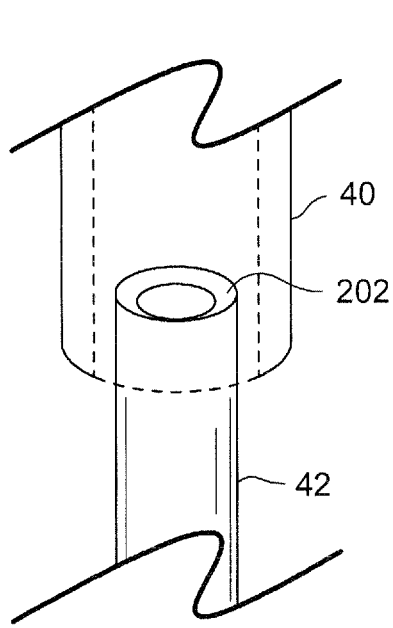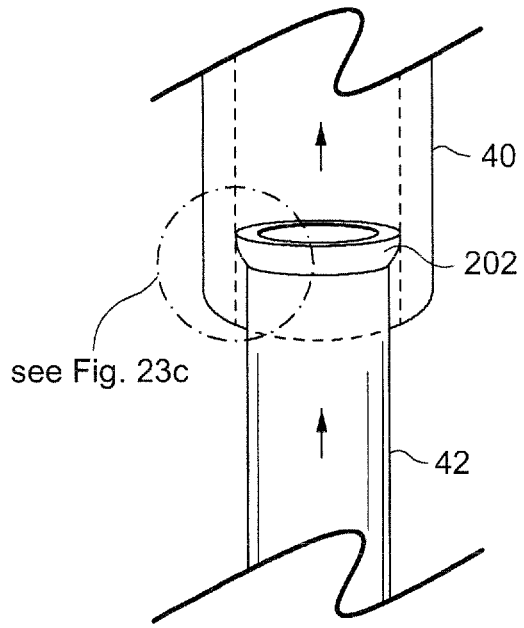
Fig. 23a  Fig. 23b
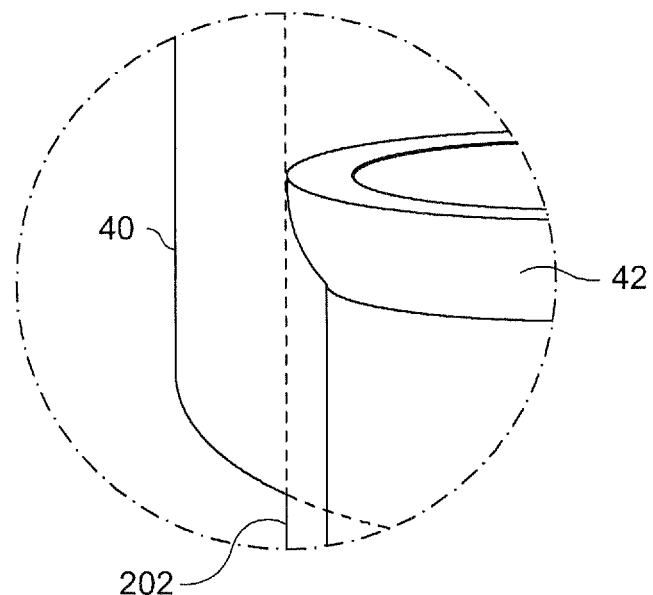
Fig. 23c

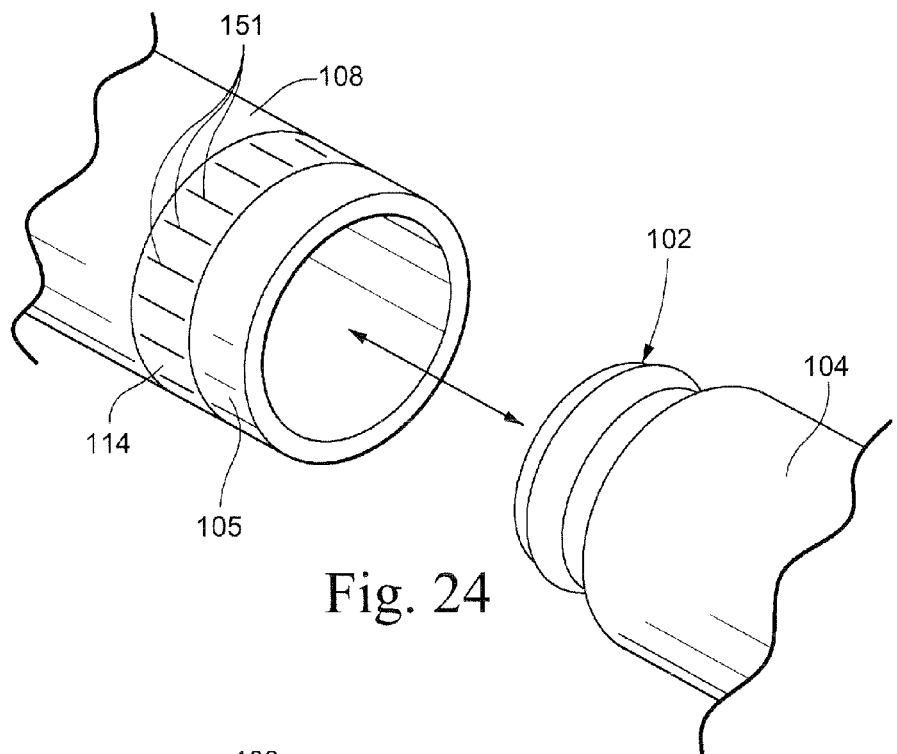
Fig. 24
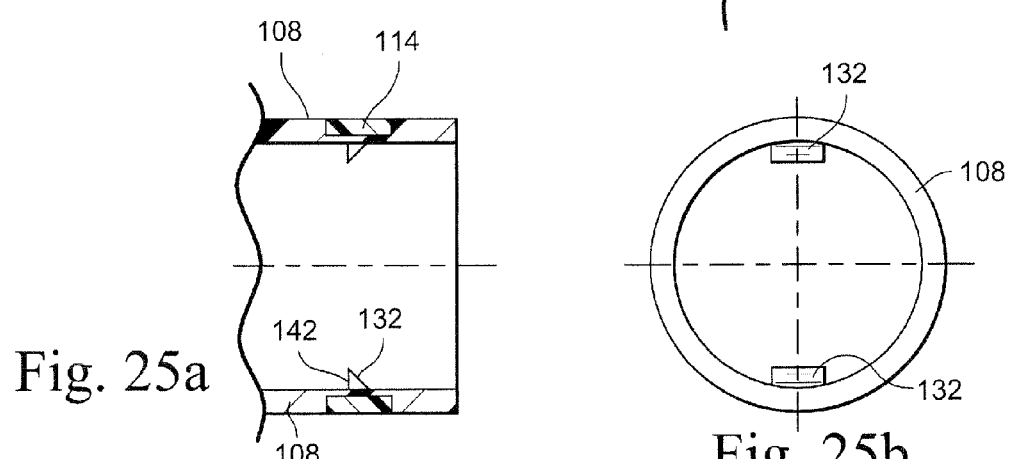
Fig. 25a
Fig. 25b
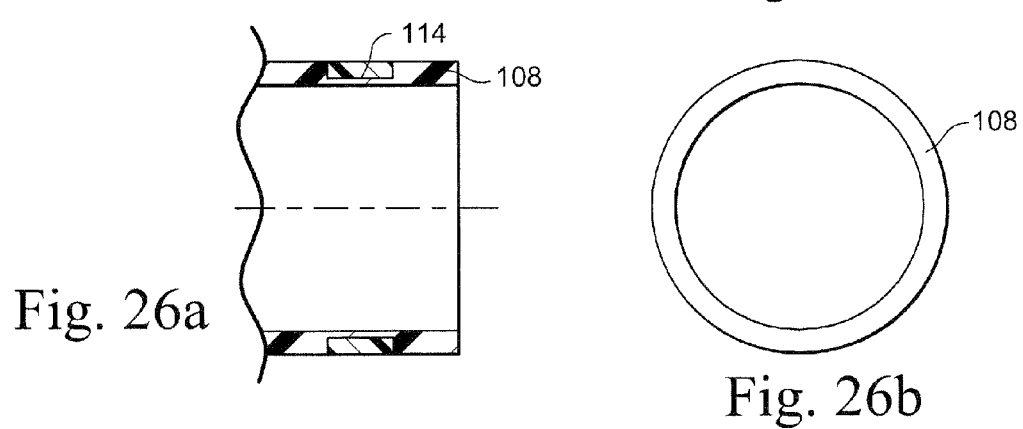
Fig. 26a
Fig. 26b

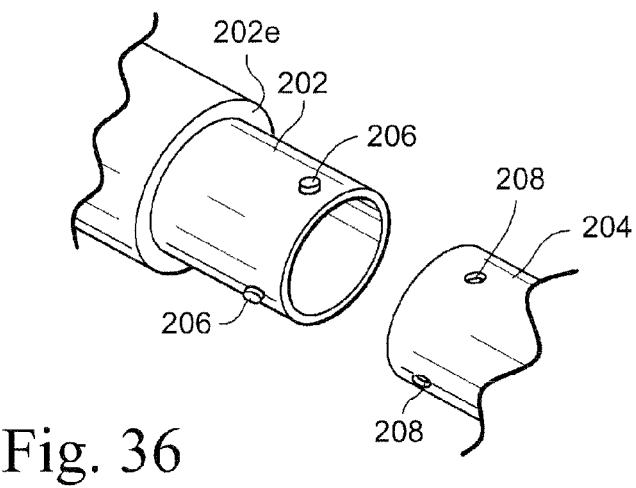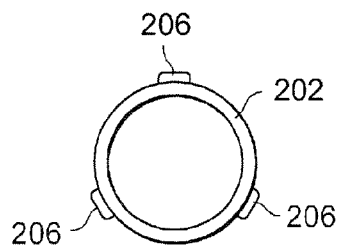
Fig. 36  Fig. 37
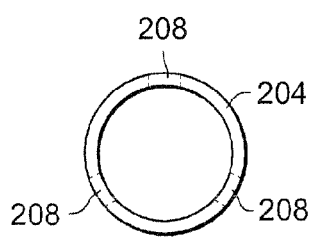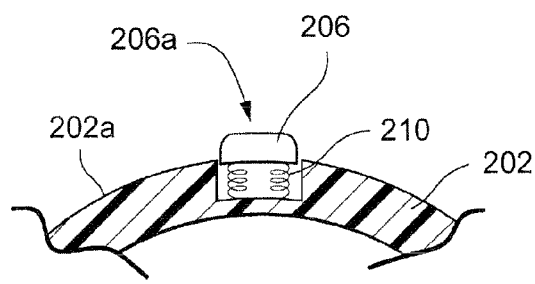
Fig. 38  Fig. 39
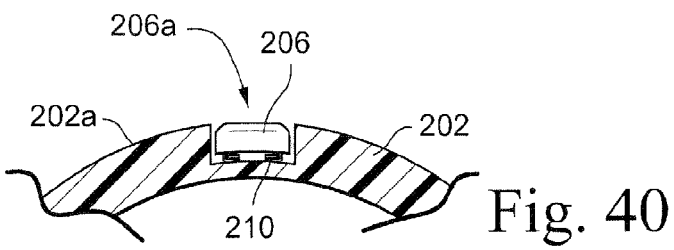
Fig. 40
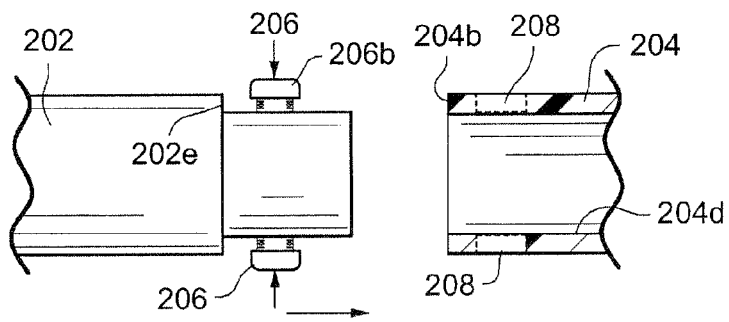
Fig. 41

CONNECTORS FOR CONNECTING COMPONENTS OF A BREATHING APPARATUS

CROSS REFERENCE TO RELATED APPLICATIONS

This application claims priority to U.S. Applications Nos. 60/907,971, filed Apr. 25, 2007 and 60/980,208, filed Oct. 16, 2007, the entire contents of both being incorporated herein by reference in their entirety.

FIELD OF THE INVENTION

The present invention relates to connectors for connecting components of a breathing apparatus.

BACKGROUND OF THE INVENTION

Breathing apparatus to deliver breathable gas to a patient typically includes a flow generator, an air delivery conduit, and a patient interface (e.g. a mask). In use, the air delivery conduit delivers pressurized gas from the flow generator to the patient interface in communication with the patient's upper airways for treatment, e.g., of Sleep Disordered Breathing (SDB) with Positive Airway Pressure (PAP), Continuous Positive Airway Pressure (CPAP) or Non-Invasive Positive Pressure Ventilation (NIPPV) devices.

To provide effective and efficient therapy, the connections between all of the components in the gas delivery pathway should be substantially leakproof. Current connectors in breathing apparatus include cylindrical rubber connectors at the inlets and outlets of the components to be connected in series in a socket configuration. The diameter of a cylindrical rubber connector on a connecting end of a component must be large enough to allow relative sliding with a connecting end of a connecting component, but small enough to allow contact between the two cylindrical rubber connectors. The rubber connectors must also be stiff enough to maintain their structural integrity so as to maintain a leakproof connection and seal, while providing some degree of flexibility. The seal is formed where the inner circumferential surface of the larger diameter connector holds the outer circumferential surface of the smaller diameter connector. Friction between the connectors inhibits excessive movement between the two connectors and prevents disconnection unless an external force is applied.

The current connectors used in breathing apparatus do not permit rapid assembly of the components because of the friction between the rubber connectors. The current connectors also limit the freedom of movement of the components at the connection points. The stability of the current connectors is also proportional to the length of the connectors, and more stable connections require longer connectors, thus increasing the size of the components of the gas delivery pathway. The current connectors are also passive, and do not adapt well to movement of components of the gas delivery pathway or act to maintain the connection.

SUMMARY OF THE INVENTION

One sample embodiment of the invention comprises a connector for connecting components of a breathing apparatus. The components include at least a flow generator to generate a flow of breathable gas, a patient interface, and a delivery conduit to deliver the breathable gas from the flow generator to the patient interface. The connector comprises a male connector extending from an end of a first component, the male connector comprising a recess; a female connector extending from an end of a second component, the female connector comprising a lever pivotally connected thereto. The male connector is insertable into the female connector so that the lever engages the recess and connects the first and second components.

Another sample embodiment of the invention comprises a connector for connecting components of a breathing apparatus. The components include at least a flow generator to generate a flow of breathable gas, a patient interface, and a delivery conduit to deliver the breathable gas from the flow generator to the patient interface. The connector comprises a first component comprising a channel; and a second component comprising at least one retractable pin configured to engage the channel upon insertion of the first component into the second component.

Still another sample embodiment of the invention comprises a connector for connecting components of a breathing apparatus. The components include at least a flow generator to generate a flow of breathable gas, a patient interface, and a delivery conduit to deliver the breathable gas from the flow generator to the patient interface. The connector comprises a first component having at least one retractable projection extending from an outer surface; and a second component having an aperture extending through an outer surface. The first component is configured to be inserted into the second component so that the at least one retractable projection is retracted upon engagement of the first and second components, and projects into the aperture upon alignment of the at least one retractable projection and the aperture.

Another sample embodiment of the invention comprises a switch for indicating a connection state of a connector for connecting components of a breathing apparatus, the components including at least a flow generator for generating a flow of breathable gas, a patient interface, and a delivery conduit for delivering the breathable gas from the flow generator to the patient interface. The switch comprises a ring provided in an end of the first or second component, the ring comprising a projection extending through an aperture in the end of the first or second component, wherein the projection is movable between a first position that indicates a connected state of the connector, and a second position that indicates an unconnected state of the connector. The switch may be used with any of the connectors of the present invention.

Yet another sample embodiment of the invention comprises a combination of a connector and a switch.

Still another sample embodiment of the invention comprises a positive airway pressure device comprising a motor to generate a flow of gas pressurized in a range of about 4-30 cm of $H_2O$; a patient interface; an air delivery conduit between the motor and the patient interface; and a connector.

A further sample embodiment of the invention comprises a positive airway pressure device comprising a motor to generate a flow of gas pressurized in a range of about 4-30 cm of $H_2O$; a patient interface; an air delivery conduit between the motor and the patient interface; and a combination of a connector and a switch.

Another sample embodiment of the invention comprises a patient interface comprising a frame; a cushion provided to the frame; and a connector.

A still further sample embodiment of the invention comprises a patient interface comprising a frame; a cushion provided to the frame; and a combination of a connector and a switch.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of the invention. In such drawings:

FIGS. 2a and 2b illustrate a connector according to an embodiment of the invention;

FIGS. 3a and 3b illustrate a connector according to an embodiment of the invention;

FIG. 4 illustrates a connector according to an embodiment of the invention;

FIGS. 13a and 13b illustrate a connector according to an embodiment of the invention;

FIG. 14 illustrates a connector according to an embodiment of the invention;

FIGS. 23a-23c illustrate a connector according to an embodiment of the invention;

FIGS. 24-33 illustrate a tube-to-tube connector arrangement according to an embodiment of the invention;

FIG. 24 is a perspective illustration of a tube-to-tube connector arrangement according to an embodiment of the invention;

FIGS. 25a and 25b are sectional and end views, respectively, of the connector arrangement of FIG. 24 in the engaging, or locking, position;

FIGS. 26a and 26b are sectional and end views, respectively, of the connector arrangement of FIG. 24 in the disengaged, or unlocked, position;

FIGS. 27a-31b schematically illustrate the operation of the connector arrangement of FIG. 24;

FIG. 33 is an exploded assembly view of the second and third tube and the pin of the connector arrangement of FIG. 24;

FIG. 36 is a perspective view of a sample embodiment of a connector arrangement according to the invention;

FIG. 37 is an end view of a part of the connector arrangement of FIG. 36;

FIG. 38 is an end view of another part of the connector arrangement of FIG. 36;

FIG. 39 is a sectional view of the part of FIG. 37 in a disconnected configuration;

FIG. 40 is a sectional view of the part of FIG. 37 in a connected configuration;

FIG. 41 is a side view of the connector arrangement of FIG. 36;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

1.0 Overall Breathing Apparatus

Figure 1:
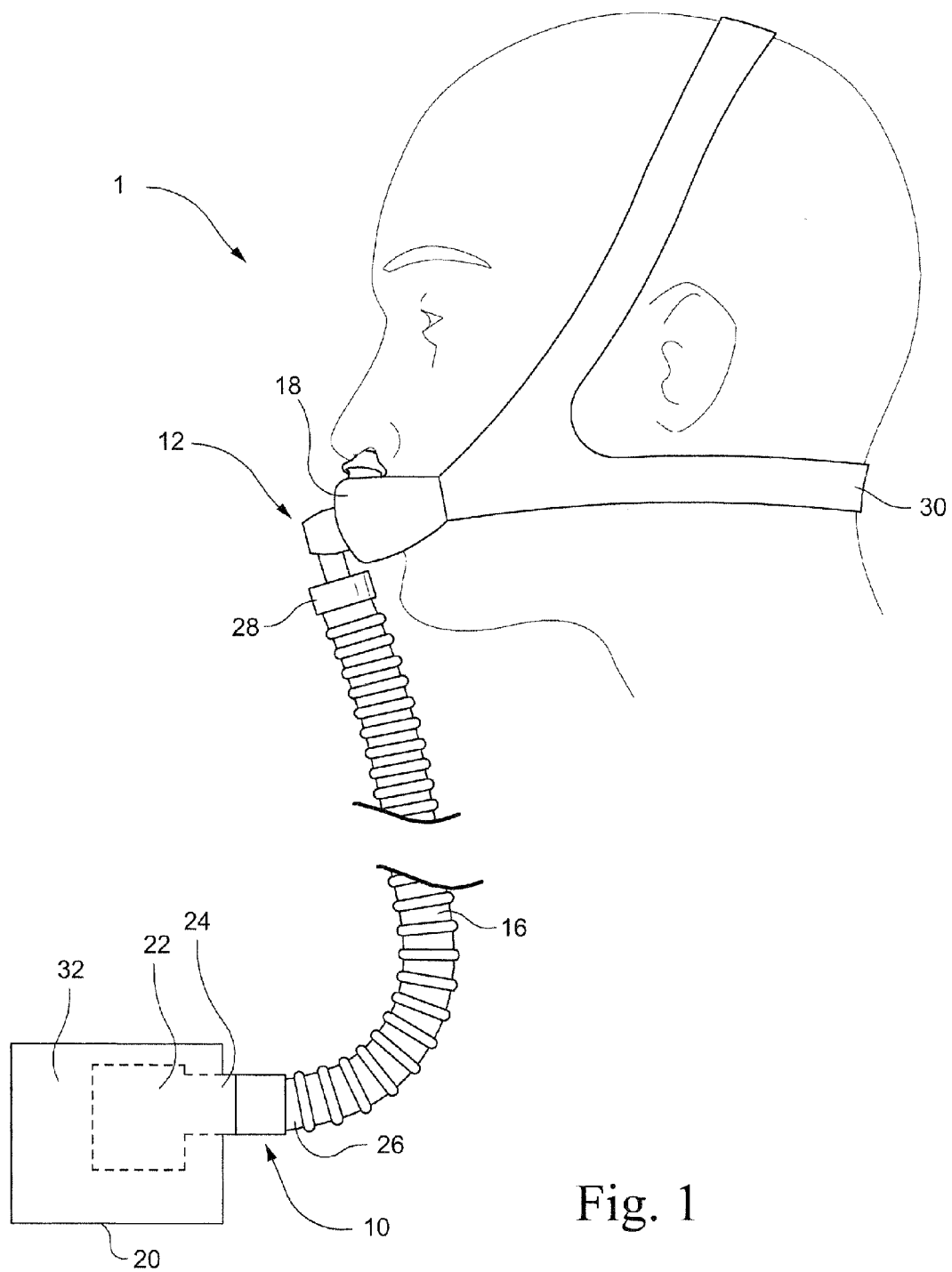
FIG. 1 illustrates a breathing apparatus for which connectors according to the invention are usable.

Referring to FIG. 1, a breathing apparatus 1 that delivers a supply of pressurized breathable air to a patient for treatment, e.g., of Sleep Disordered Breathing (SDB) with a PAP, CPAP or NIPPV device, generally includes a flow generator 15, an air delivery conduit 16, and a patient interface 18. The flow generator 15 is structured to generate a supply of pressurized air to be provided to a patient for treatment, e.g., in the pressure range of about 4-30 cm $H_2O$ at a flow of about 150-200 L/min. The flow generator 15 includes a housing 20 and a blower 22 supported within the housing 20. The blower 22 is operable to draw a supply of air into the housing 20 through one or more intake openings and provide a pressurized flow of air at an outlet 24. The supply of pressurized air is delivered to the patient via the air delivery conduit 16 that includes one end 26 coupled to the outlet 24 of the flow generator 15 at a connector 10 and an opposite end 28 coupled to the patient interface 18 at a connector 12, as shown in FIG. 1. The air delivery conduit 16 has a an inner diameter of 22 mm, but it can be larger or smaller (e.g., 15 mm).

The patient interface 18 comfortably engages the patient's face and provides a seal. The patient interface 18 may have any suitable configuration, such as a full-face mask, nasal mask, oro-nasal mask, mouth mask, nasal nozzles or prongs, etc. Patient interface 18 typically includes a frame and a cushion. Also, any suitable headgear arrangement 30 may be utilized to comfortably support the patient interface 18 in a desired position on the patient's face.

It should be appreciated that the breathing apparatus 1 may include other devices and/or components which may require additional connectors other than those illustrated in FIG. 1, such as a humidifier unit, etc. Further, such connectors can be used to connect a supplemental gas delivery conduit or pressure measuring conduit to a port provided on the patient interface.

2.0 First Embodiment

Referring to FIGS. 2a and 2b, a connector is provided between two components 40, 42 of the breathing apparatus 1. The components may be the outlet of a blower or humidifier, or a hose or conduit, or an input of a patient interface. The connector may include a gasket 44 provided at the end of each component 40, 42. The gaskets 44 may be formed of suitable material for providing a seal for the flow of breathable gas. For example, the gaskets 44 may be formed of plastic, silicone or rubber. Each gasket 44 holds a magnet 46. The magnet 46 may be held in the inner circumference of the gasket 44, as shown in FIG. 2b. It should be appreciated that the magnet 46 may, or may not, be entirely surrounded, or embedded, in the gasket 44, for example by over-molding the gasket 44 onto the magnet 46. The magnets may be ring shaped, as shown in FIGS. 2a and 2b. It should be appreciated, however, that the magnet(s) may be any shape or orientation that generates a magnetic field that assists in attracting/retaining or repelling the connection depending on the application. For example, smaller magnets may be placed around the cross sectional edge of the tubing, rather than a solid magnetic ring. Arc segments may also be used.

When the two ends of the components 40, 42 are positioned close together, the magnets 46 provide a magnetic force sufficient to assist in generating a connection between the components 40, 42. In one sample embodiment, the magnetic attraction may act as the primary method of retaining the connection. The gaskets 44 seal the connector to provide a substantially leakproof connection for the flow of breathable gas.

2.1 Second Embodiment

Referring to FIGS. 3a and 3b, in another embodiment, the components 40, 42 may be connected using an additional connecting piece 48. The connecting piece 48 may include a magnet 50 which is surrounded by, or embedded in, a gasket 52. When using a connecting piece 48, the magnet 46 at both ends of the connector may be replaced by a magnet and a ferromagnetic material that is readily attracted to the magnet of the connecting piece 48. In this configuration, both connecting ends will not be actively attracted towards each other without a connecting piece 48 that contains a magnet. The connecting piece 48 will act as a control or actuator for a connection to be achieved.

When the connectors are not in use, all of the connecting pieces 48 along the air delivery pathway can be positioned adjacent to each other to form a stack of connecting pieces, where each piece contains a magnet. This configuration provides a more convenient form of storing the connecting pieces when not in use, at the same time avoiding accidental magnetic attraction. This configuration would be useful where space is limited, for example in luggage during traveling.

2.2 Third Embodiment

As shown in FIG. 4, in a further embodiment, the connecting piece 48 may include edges 54 that extend over the ends of the components 40, 42 to provide a larger sealed area at the connection.

2.3 Fourth Embodiment

Figure 5A:
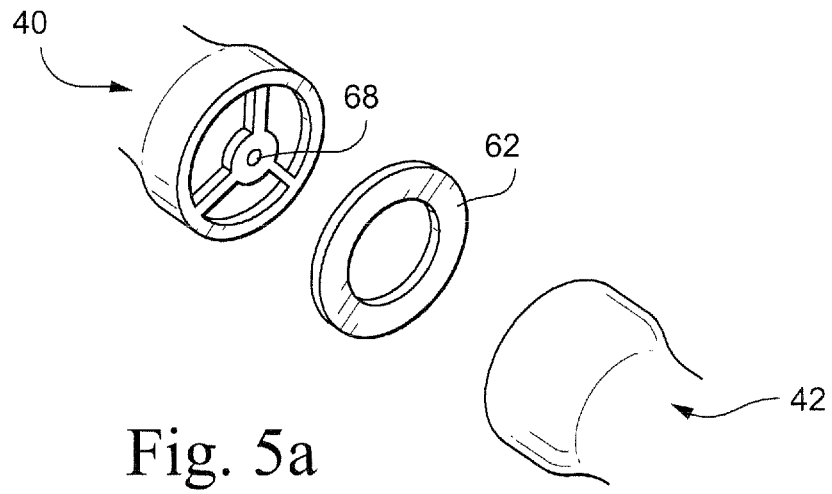
FIGS. 5a-5c illustrate a connector according to an embodiment of the invention.
Figure 5B:
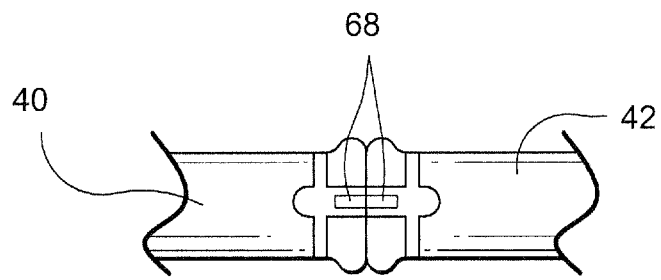
Figure 5C:
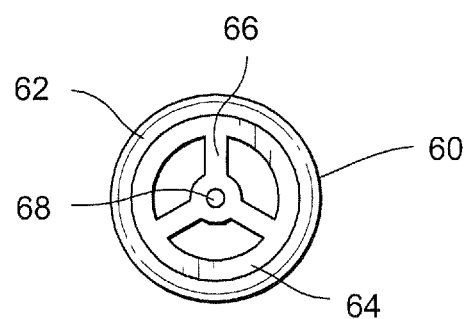

According to another embodiment shown in FIGS. 5a-5c, seals 60 may be provided between the components 40, 42. Each seal 60 includes a seal cover 62. A supporting ring 64 is surrounded by the seal cover 62. The supporting ring 64 includes supporting arms 66 that support a magnet 68 in a center of the supporting ring 64. The components 40, 42 are connected by the attraction of the magnets 68 and the connection is sealed by the seal covers 62. The components 40, 42 may be rotated relative to one another without breaking the connection between the magnets 68.

In the embodiment shown in FIGS. 5a-5c, as the magnets 68 are provided in the center of the connection, the seals are more easily located around the periphery of the connection. Locating the magnet in the center of the connection shields the magnet as it is located away from the surface. Other methods of magnetic shielding may also be used or included into the concentric components surrounding the magnet. The connection is also magnetically shielded as the magnets 68 are effectively encased in the components 40, 42. The magnets may also be smaller than the magnets used in the embodiments shown in FIGS. 2-4.

2.4 Fifth Embodiment

Figure 6:
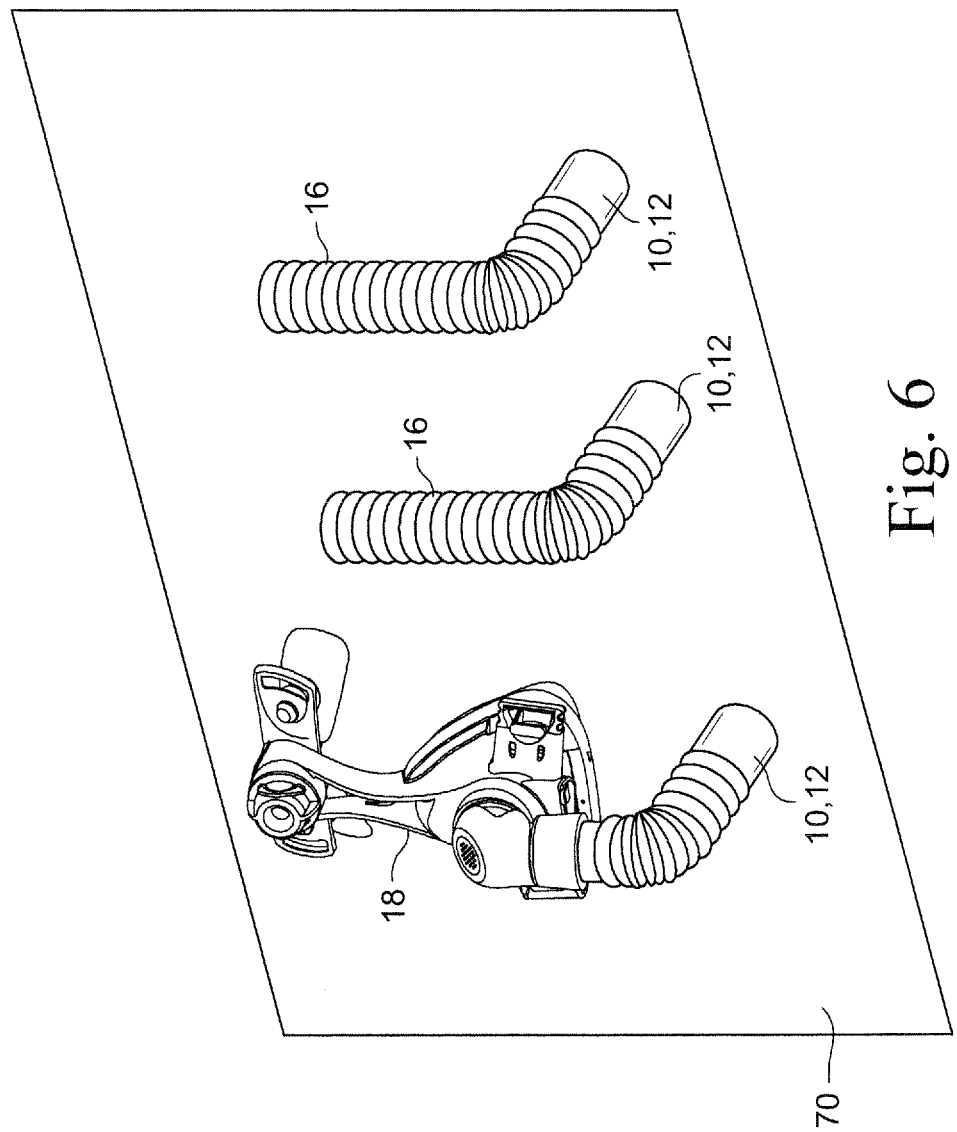
FIG. 6 illustrates a storage system for components of a breathing apparatus using connectors according to the invention.

Referring to FIG. 6, a support 70, such as a plate or board, may include connectors 10, 12. The connectors may be any of those discussed above with respect to FIGS. 2a-9. The connectors 10, 12 allow air delivery conduits 16 and patient interfaces 18 to be supported by the support 70 for quick storage and access, for example by clinical or medical personnel or the patient. The support 70 may also be used during a cleaning process and enable components to be cleaned and dried more easily and efficiently by holding them in the correct and convenient position.

2.5 Sixth Embodiment

As shown in FIGS. 7a-7d, two components 40, 42 of the breathing apparatus may be connected by a connector including a soft, flexible member 72, 74 provided to the end of each component 40, 42, respectively. The soft, flexible members 72, 74 may be formed, for example, of silicone. The soft, flexible members 72, 74 are provided around the components 40, 42 so as not to limit the flexibility of the components 40, 42, which may be, for example, delivery conduits. The soft, flexible members 72, 74 may also include contours or grooves or hand grips, as shown FIGS. 7a-7d to provide for better handling by the user of the breathing apparatus or clinical/medical personnel.

Figure 7A:
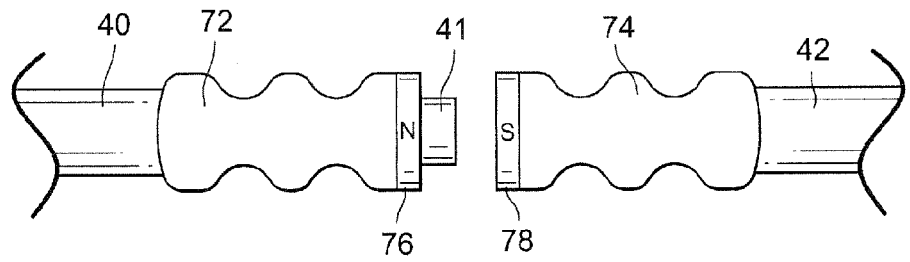
FIGS. 7a-7d illustrate a connector according to an embodiment of the invention.
Figure 7B:
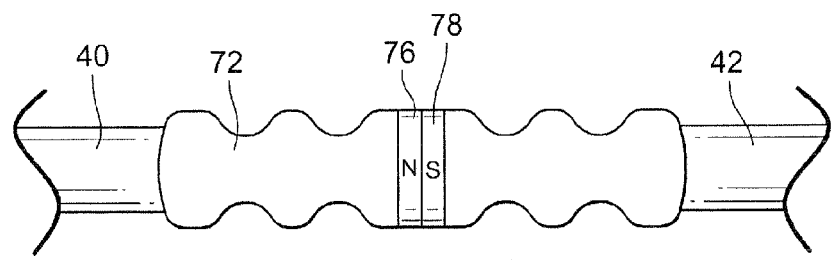
Figure 7C:
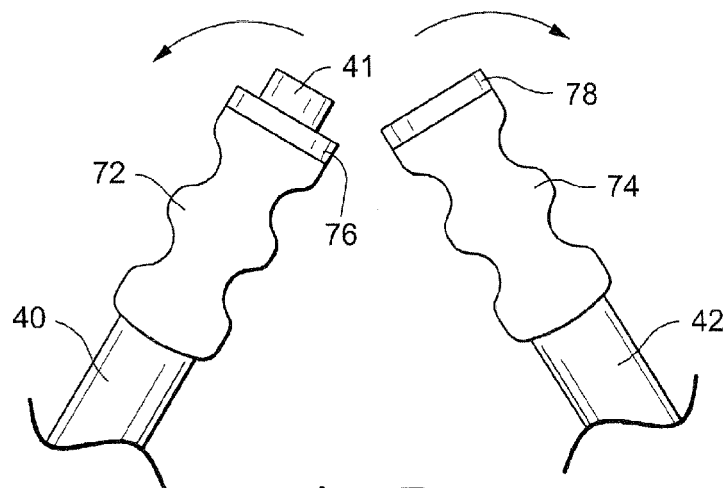

Each soft, flexible member 72, 74 has a magnet 76, 78, respectively, at its end. The magnets 76, 78 are attracted to one another and provide a connection between the components 40, 42 when the magnetic attraction between the magnets 76, 78 to contact one another. The magnetic attraction provides a connection, as shown in FIG. 7b, that is difficult to disconnect by a tensile force, i.e. a force along the axial direction of the components, but which can be disconnected by snapping open as shown in FIG. 7c. As also shown in FIG. 7c, the end 41 of the component 40 may be smaller, or tapered, to permit the connector to be flexible and disconnectable by snapping the magnets 76, 78 apart. Smaller end 41 is inserted into the opposite connector and helps with the disconnect of the magnets and/or conduits and/or paths. The length of the end 41 may be increased so that it hinders disconnection by not allowing the snapping motion depicted in FIG. 7c to occur. This would allow the magnetic retention force required to maintain the connection.

Figure 7D:
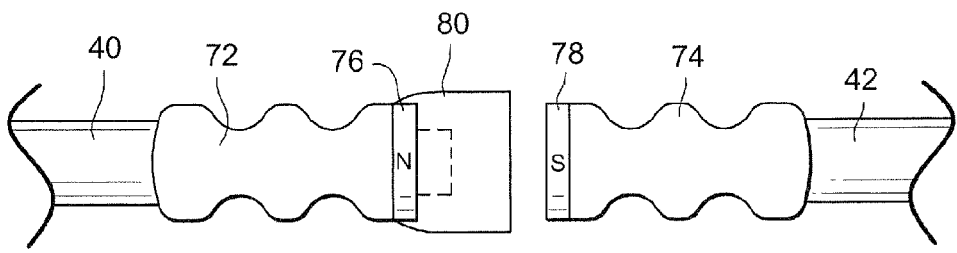

In order to prevent a user's fingers from being pinched between the magnets 76, 78, a connector cover 80 may be provided as shown in FIG. 7d. It should be appreciated that the cover 80 may be provided to either component 40, 42, or to both components. The connector cover 80 may also act to shield the magnets and increase the attraction and retention force between the two members 72, 74.

The connection formed by the magnetic attraction between the magnets 76, 78 may be supplemented by a lock mechanism, as described in more detail below. The use of a lock mechanism may also be provided to any of the connectors described above, or in more detail below.

2.6 Seventh Embodiment

Figure 8:
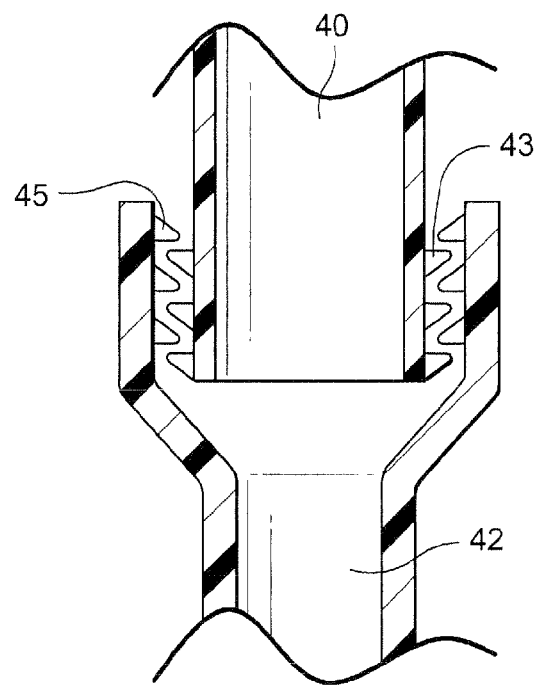
FIG. 8 illustrates a lock mechanism usable with connectors according to the invention.

Referring to FIG. 8, a lock mechanism may include teeth 43 on the end of component 40 that engage teeth 45 on the end of component 42 when the end of component 40 is inserted into the end of component 42. The teeth 43, 45 are flexible enough to permit the insertion and removal on the end of component 40 into the end of component 42, but provide sufficient resistance to disconnection to maintain the connection between components 40, 42 during normal use. The ends of the components 40, 42 are sufficiently stiff or rigid to permit insertion and establishment of the connection. However, the ends are not so rigid as to prevent the ends of the components from being disconnected by, for example, twisting the ends. It should also be appreciated that the ends of the component may be connectable and disconnectable by threaded engagement.

2.7 Eighth Embodiment

Figure 9A:
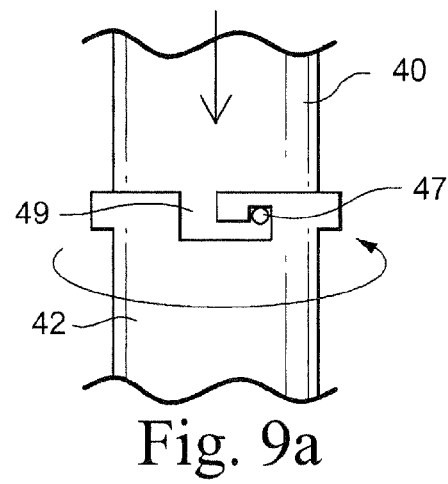
FIGS. 9a-9c illustrate a connector according to an embodiment of the invention.
Figure 9B:
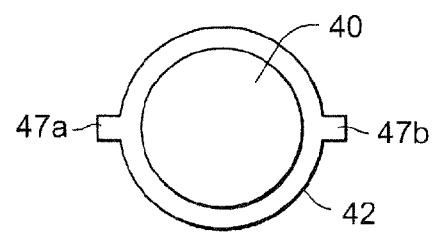

As shown in FIG. 9a, the lock mechanism may be a twist lock mechanism, such as a bayonet connection. The end of component 40 includes a projection 47 that is inserted in a slot 49 in the end of component 42. Although not shown in the drawings, it should be appreciated that either, or both, ends of the components 40, 42 may be tapered or sloped to facilitate the insertion. The connection is completed by rotating the components 40, 42 relative to each other as shown by the arrow in FIG. 9a. As shown in FIG. 9b, the bayonet connection may be formed by one or more projections 47a, 47b on component 40 that are received in one or more respective slots in component 42. This configuration may be used in a case where the connection of the components 40, 42 requires a particular alignment for the connection.

Figure 9C:
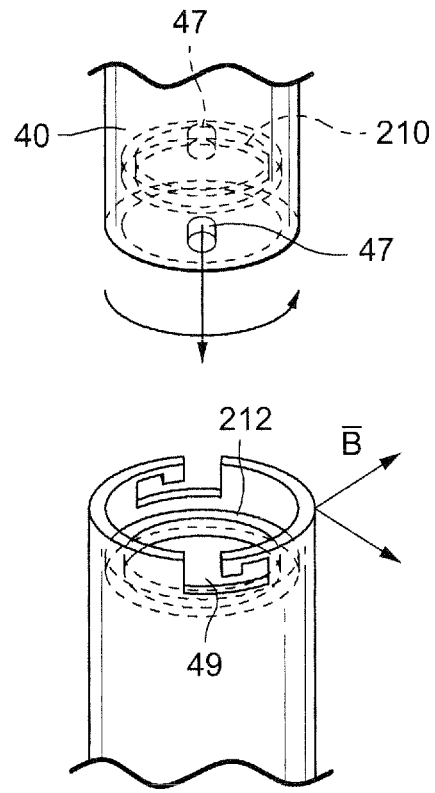

Magnets 210, 212, or a magnet and a ferromagnetic ring, may be provided in the ends of the components 40, 42, respectively, as shown in FIG. 9c to attract the projection(s) 47 into the locking position in the slot(s) 49. Such an arrangement would allow establishment of the connection by a single action of the user, i.e., insertion of the projection 47 of the end of component 40 into the slot 49 in the end of component 42. The second action needed to complete establishment of the connection, i.e., the relative rotation of the components 40, 42, would be achieved, in this sample embodiment, automatically by the attraction of the magnets. In other variant sample embodiments, the rotation may be achieved by torsional force from the operator and the magnets may assist in the insertion of the projection(s) 47 in the end of the component 42 through magnetic attraction. The magnets 210, 212 may be arranged such that the resulting magnetic field(s) B causes rotation of the components relative to each other into the connected and sealed position.

2.8 Ninth Embodiment

Figure 10A:
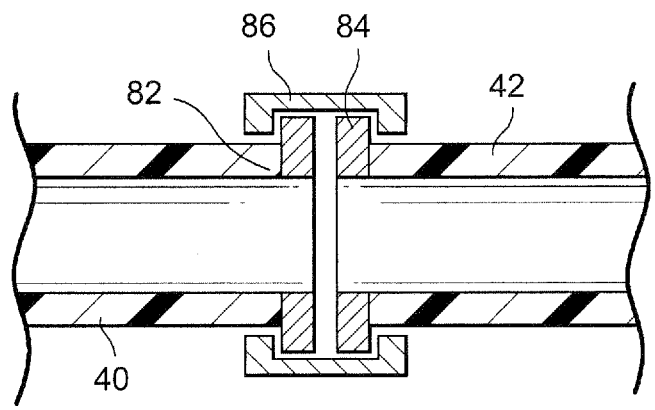
FIGS. 10a and 10b illustrate a connector according to an embodiment of the invention.
Figure 10B:
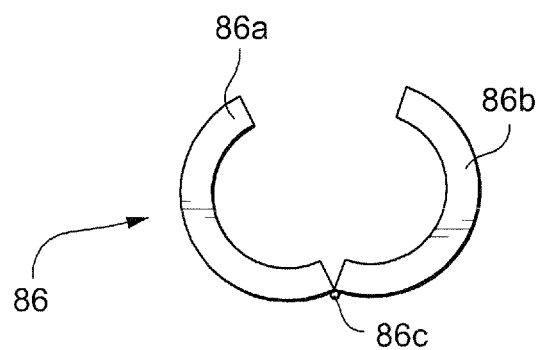

Referring to FIGS. 10a and 10b, a connector may include magnets 82, 84 provided at ends of components 40, 42, respectively. A clamp 86 may also be provided around the ends of the components 40, 42 to cover and secure the connection established by the magnets 82, 84. As shown in FIG. 10b, the clamp 86 may include two arms 86a, 86b connected together by a hinge 86c, e.g. a living hinge, and the ends of arms 86a, 86b may include a locking mechanism. The clamp may be integrated into components 40, 42, or it may be a separate, removable component. The clamp 86 may also be magnetic, or formed of ferromagnetic material so as to be attracted to the magnets 82, 84, so that the clamp 86 may remain attached to the connector even when not engaged or locked. The clamp may also take the form of an elastic sleeve that is stretched over the connector.

2.9 Tenth Embodiment

Figure 11:
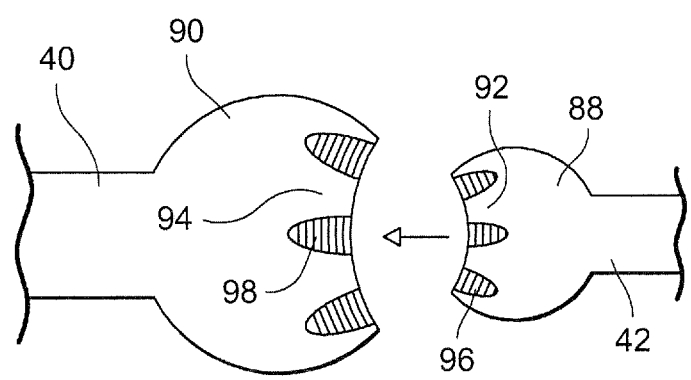
FIG. 11 illustrates a connector according to an embodiment of the invention.

A connector according to the present invention may also be formed as a ball and socket type connection. As shown in FIG. 11, the end of component 40 may be fashioned as a socket 90, and the end of component 42 may be fashioned as a ball 88. The socket 90 includes flexible fingers 94 that move radially outwardly (i.e. expand) as the ball 88 is inserted. The ball 88 includes flexible fingers 92 that move radially inwardly (i.e. contract) as the ball is inserted into socket 90. Once the ball 88 is fully inserted into the socket 90, the fingers 92, 94 return to their original configurations.

Flexible membranes 96, 98 (e.g. elastomers) are provided to the ball 88 and socket 90, respectively, to provide a substantially leakproof connection. The membranes 96, 98 may be provided around the entire inner circumferences of the ball 88 and socket 90, respectively, or the membranes 96, 98 may be provided only between the flexible fingers 92, 94. The flexible membranes 96, 98 may be integrally formed with the components 40, 42, or may be separately formed and attached to the components 40, 42 in an integrated manner.

The connector shown in FIG. 11 may be provided between the components 40, 42, such as between the outlet of the blower and the inlet of the air delivery conduit 16, or between the outlet of the air delivery conduit 16 and the inlet of the patient interface 18. The connector shown in FIG. 11 provides a high disconnection force and excellent freedom and range of motion. It should also be appreciated that the connector shown in FIG. 11 may be used at other points in the breathing apparatus to provide improved freedom and range of motion to other components of the system.

2.10 Eleventh Embodiment

Figure 12A:
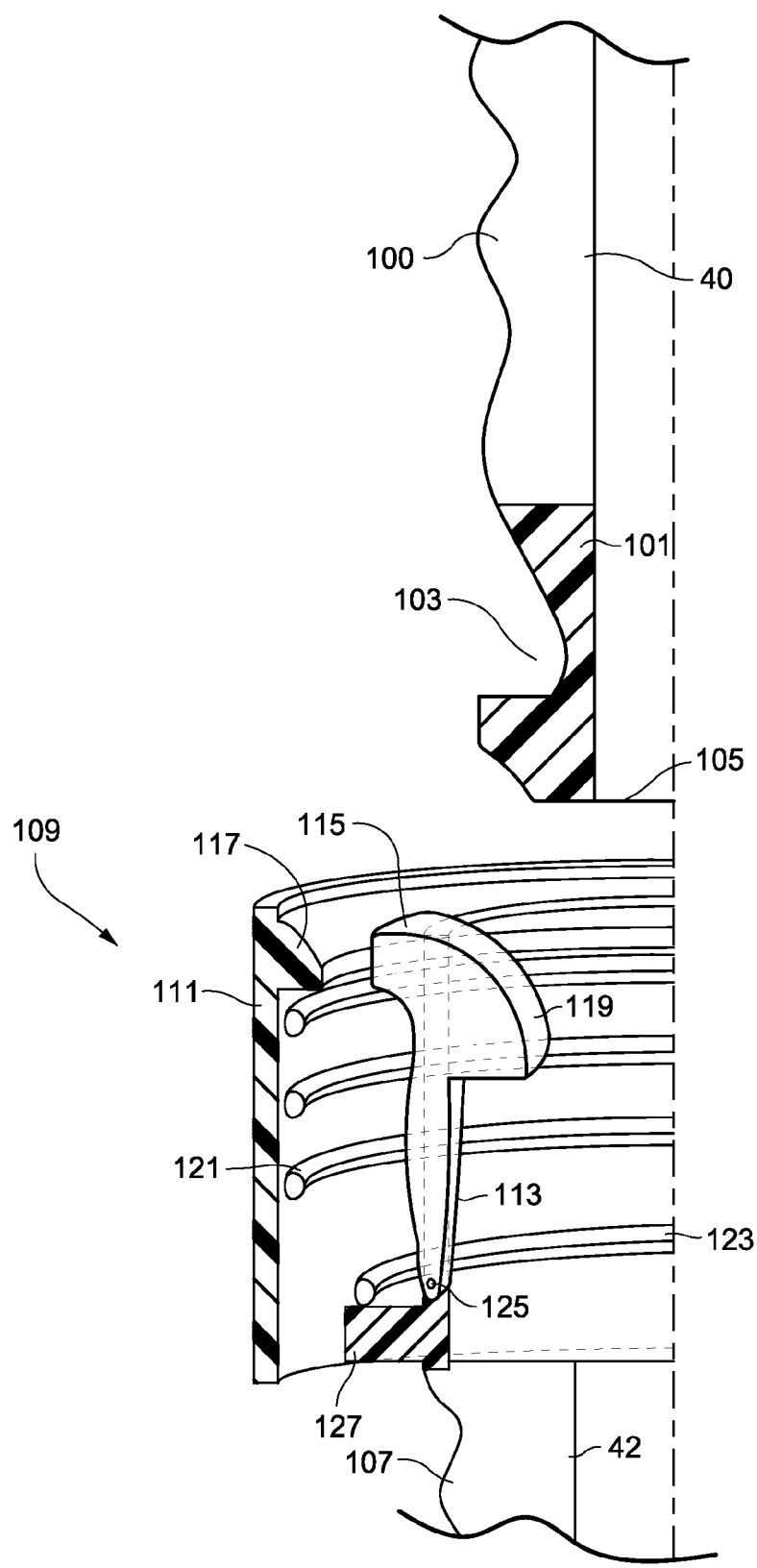
FIGS. 12a-12i illustrate a connector according to an embodiment of the invention.

Referring to FIGS. 12a-12g, the component 40 in this sample embodiment may include a grip handle 100 and a male connector 101 provided at the end 105. The component 42 in this sample embodiment may include a grip handle 107 and a female connector 109 provided at the end. The male connector 101 of the component 40 is inserted into female connector 109 of the component 42. A lever, or latch, 113 is connected to an inner casing 127 of the female connector 109 at a hinge joint, or pivot point 125. The lever 113 is biased to pivot in a counterclockwise direction by pre-loaded hinge joint at connector 109 or other spring-like element. A first spring 123 provided between the inner casing 127 and the lever 113 may achieve the same result. As shown in FIG. 12a, a projection 117 on an outer casing 111 of the female connector 109 is adjacent to and engages a second projection 115 on the lever 113 to prevent the lever 113 from pivoting counterclockwise under the bias of the pre-loaded hinge.

A second spring, or spring-like element, 121 is provided between the inner casing 127 and the outer casing 111. The second spring 121, in equilibrium, holds the outer casing 111 in the position shown in FIG. 12a, and resists movement of the outer casing 111 in an axial downwards (relative to the drawing figure) direction. It should be appreciated that the first spring 123 and the second spring 121 may be formed as an integral spring.

Figure 12B:
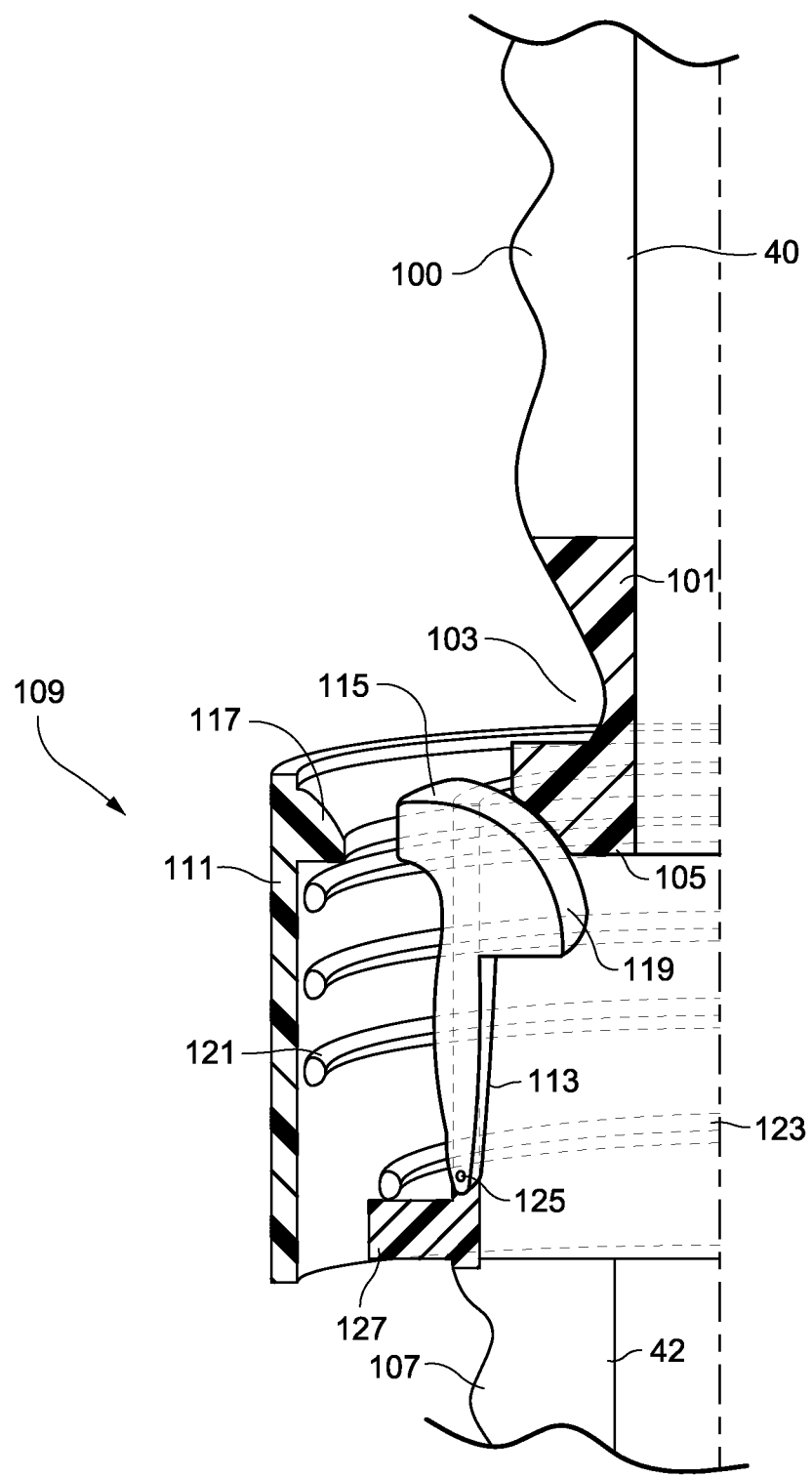
Figure 12C:
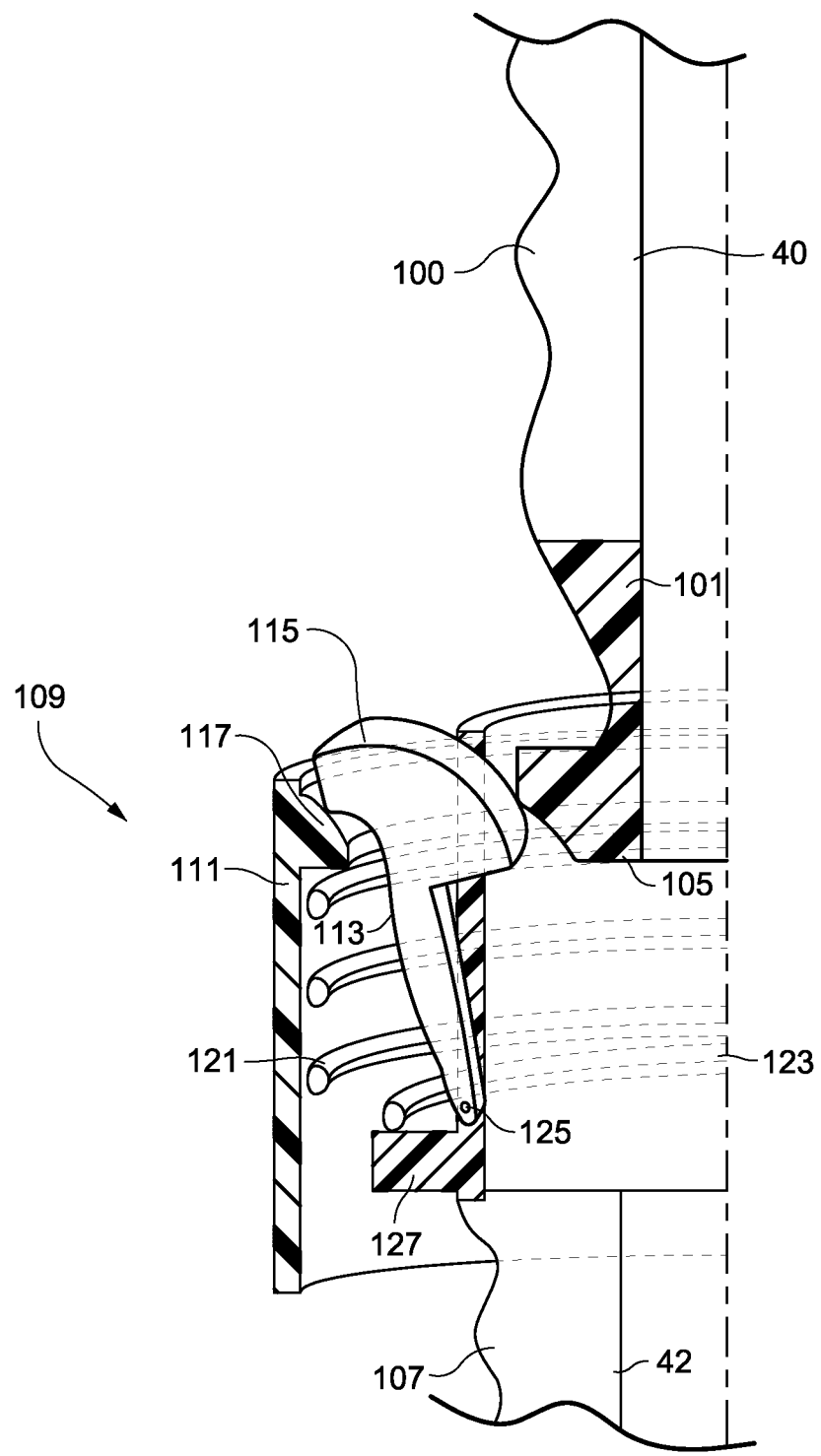
Figure 12D:
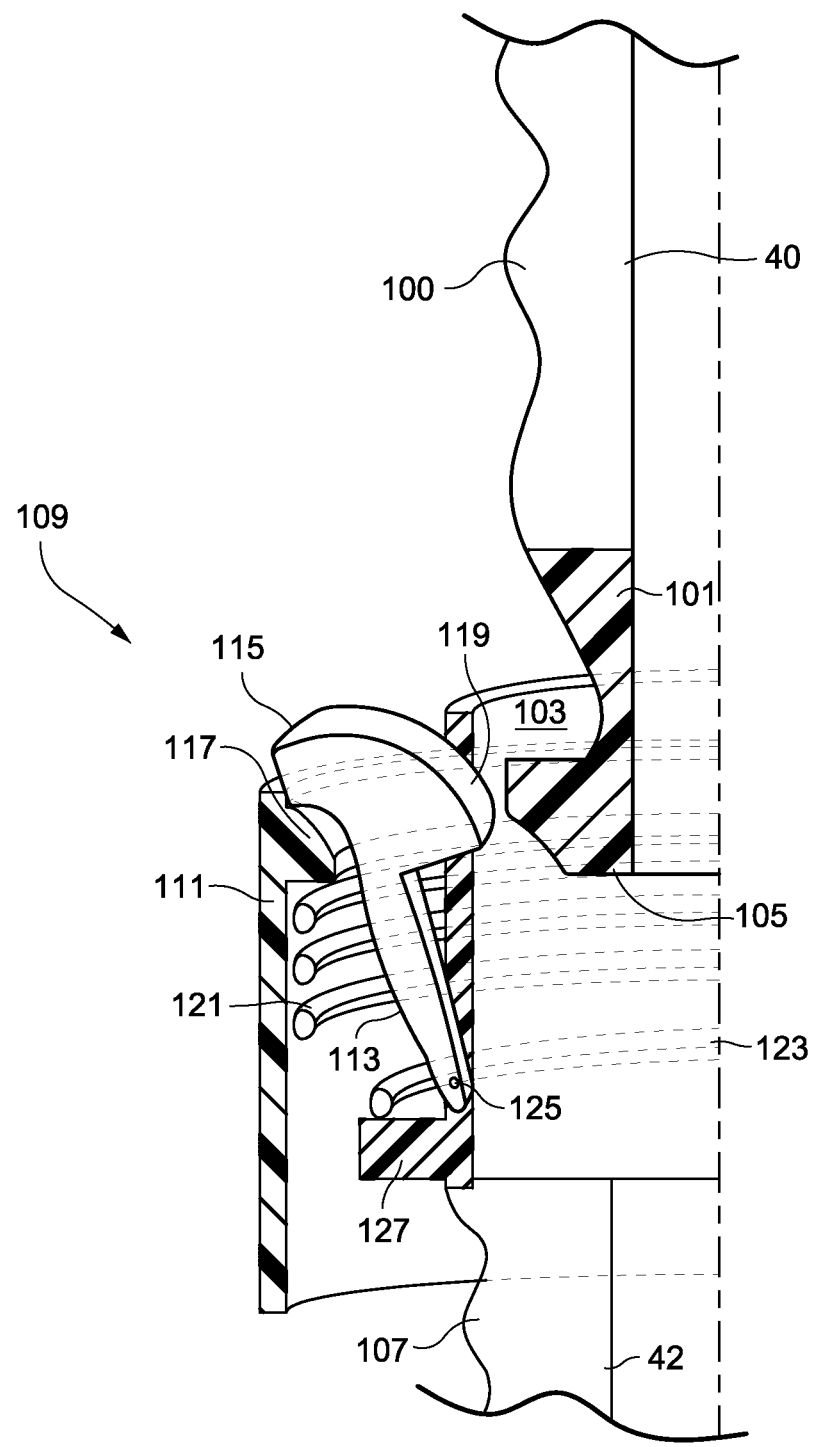

To connect the first component 40 to the second component 42, the male connector 101 is inserted into the female connector 109. As shown in FIG. 12b, upon insertion of the male connector 101 into the female connector 109, the end 105 of the male connector 101 engages and slides over a first projection 119 of the lever 113. The male connector 101 may be formed of a material that is capable of deforming as the male connector 101 is inserted into the female connector 109 and the end 105 of the male connector 101 engages and slides over the first projection 119. Alternatively, as the male connector 101 is inserted into the female connector 109, the end 105 forces the lever to move in a counter-clockwise direction as the end 105 and the first projection 119 engage, as shown in FIG. 12b. The lever 113 then acts upon the projection 117 on the outer casing 111 to move downwardly in an axial direction.

Figure 12E:
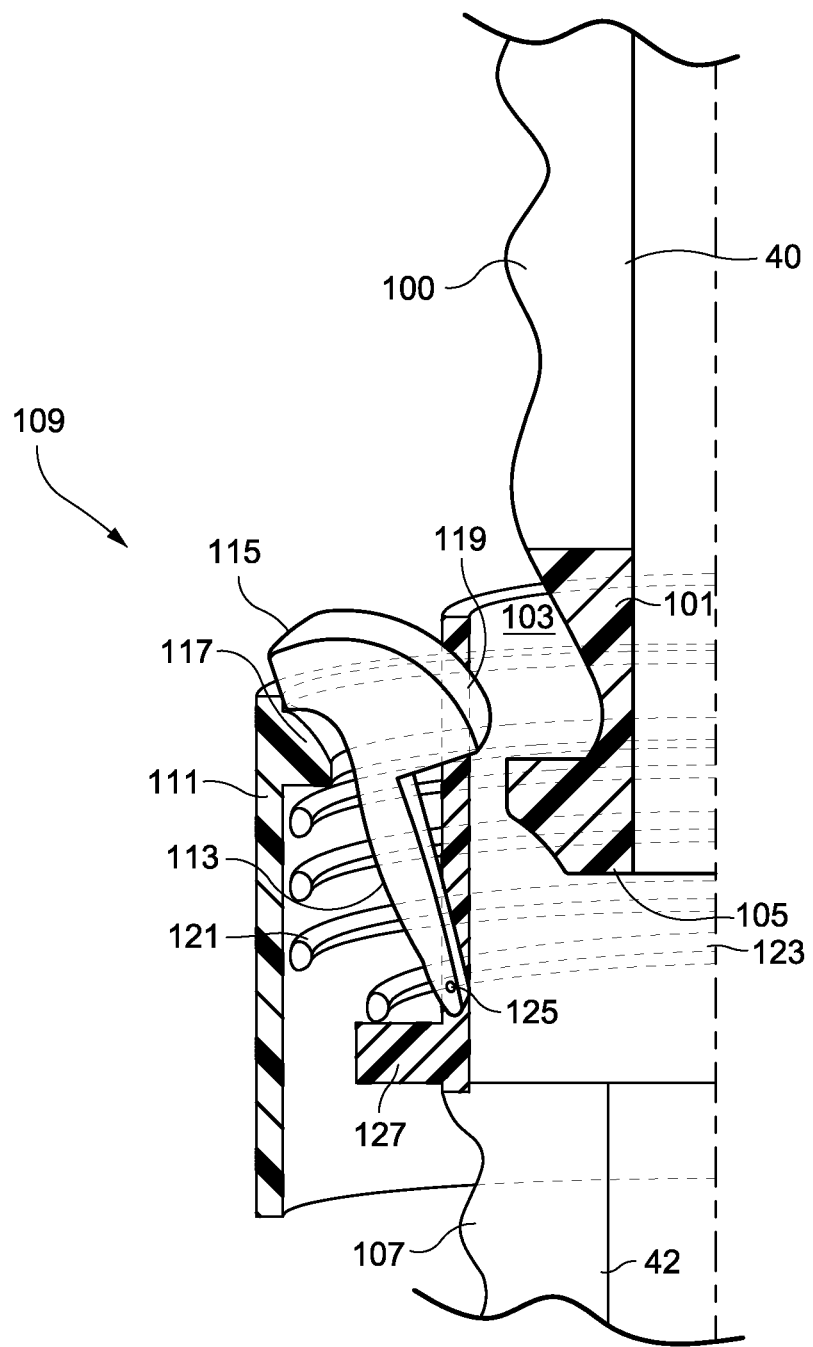
Figure 12F:
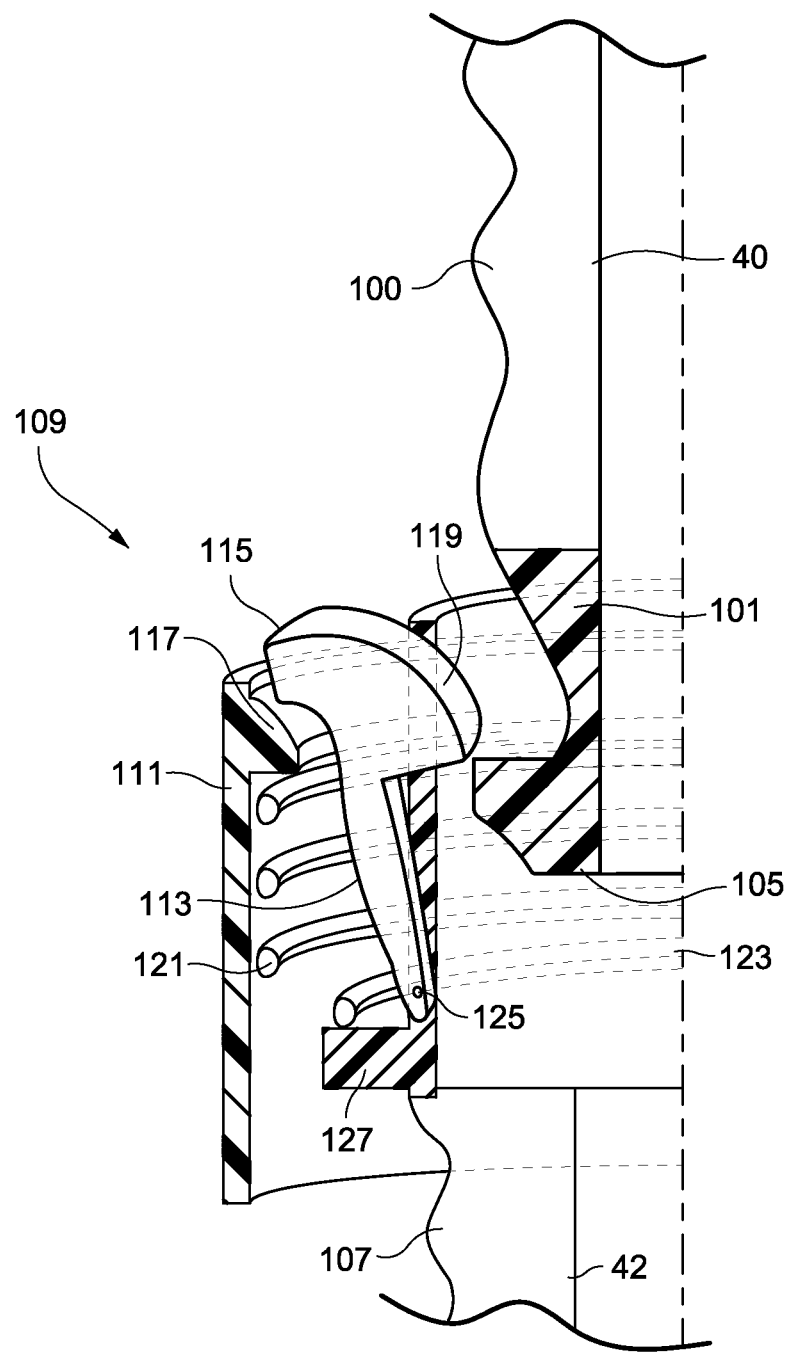
Figure 12G:
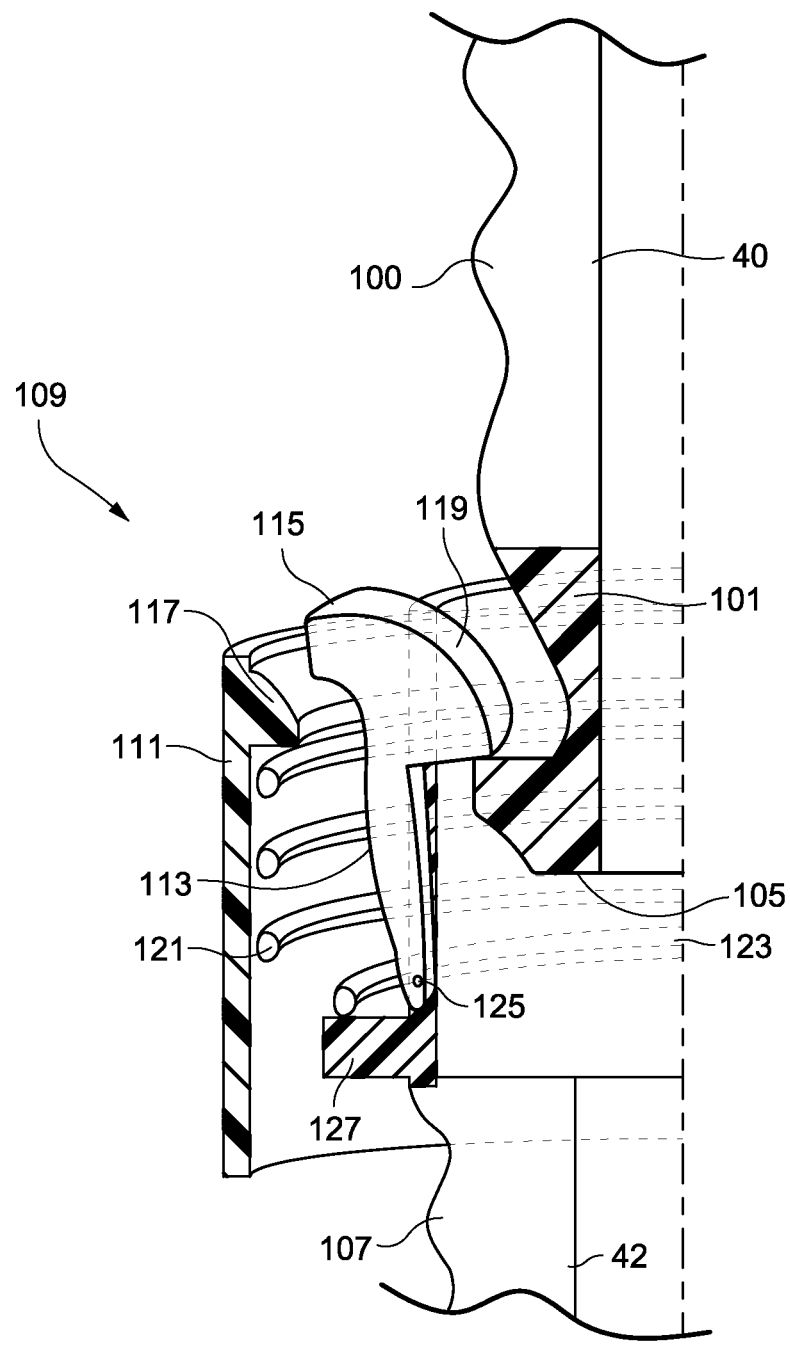
Figure 12H:
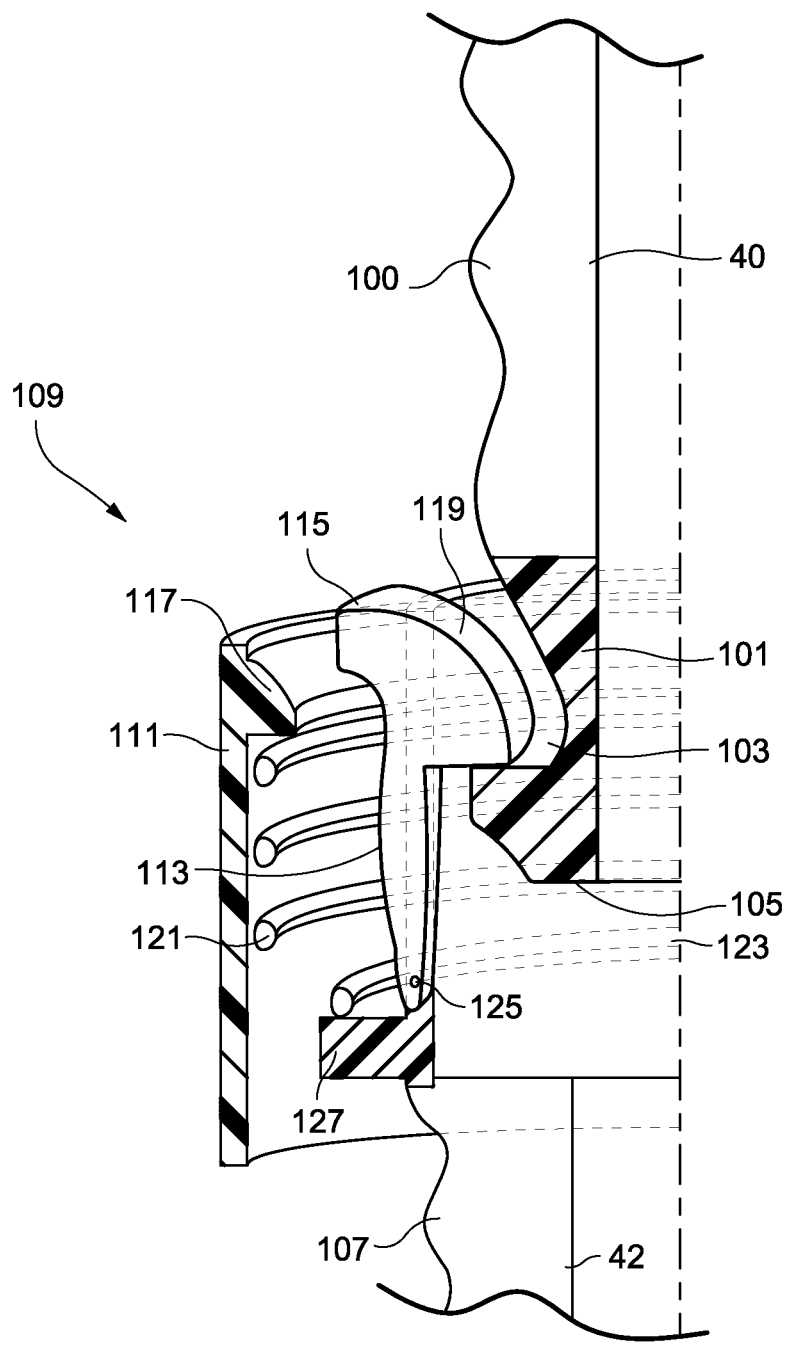
Figure 12I:
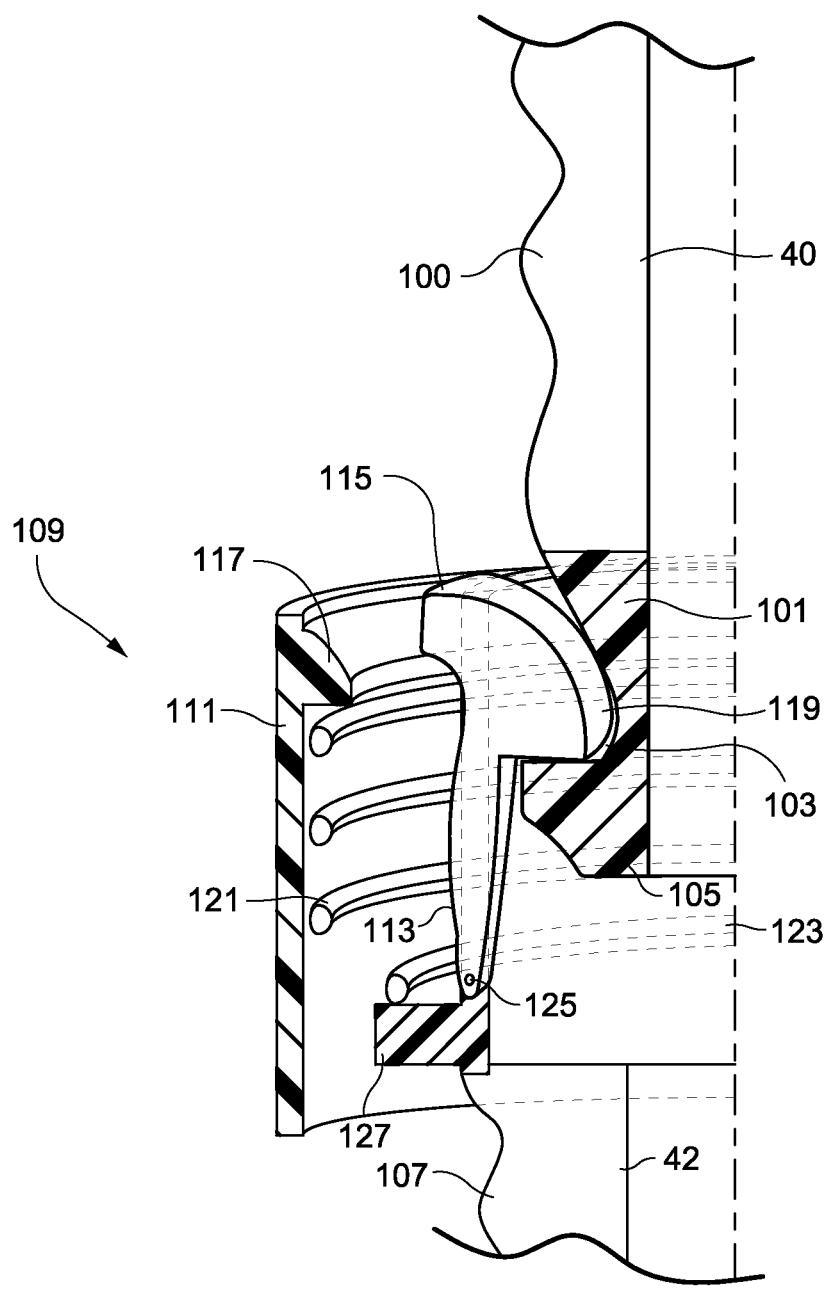

As shown in FIGS. 12e-12g, once the end 105 of the male connector 101 is inserted past the first projection 119 of the lever 113, the outer casing 111 begins to return to the equilibrium position by the force of the second spring 121. The outer casing 111 moves in the axially upward direction (relative to the drawing figure) so that the lever 113 is pivoted in the clockwise direction and the first projection 119 engages a recess 103 in the end 105 of the male connector 101. The components 40, 42 are in the connected position shown in FIG. 12g.

To disconnect the components 40, 42, the user applies a downward axial force (relative to the drawing figure) on the outer casing 111 to overcome the biasing force of the first spring 123 and the second spring 121. The projection 117 on the outer casing 111 is no longer adjacent to the second projection 115 of the lever 113 and the biasing force of the first spring 123 causes the lever 113 to pivot counterclockwise about the pivot point 125 until the first projection 119 of the lever 113 is no longer engaged in the recess 103 of the male connector 101. The male connector 101 can be disengaged from the female connector 109 by applying an upward axial force (relative to the drawing figure) on the first component 40.

The connection force of the connector of FIGS. 12a-12g may be controlled by the forces of the springs 121 and/or 123 of the female connector 109, and/or by the depth of the recess 103, and/or by the flexibility of the end 105 of the male connector 102. The female connector 109 can also be made with large gaps between the inner and outer casings to make the connector easier to clean. Magnets may also be provided at the ends of the components 40, 42 to assist the initial connection of the components.

2.11 Twelfth Embodiment

Referring to FIG. 13a, a connector includes a sleeve 128 having a locking lever 130 that has a first end 132 configured to locking engage a projection 138 on an end of component 40. Although not shown, it should be appreciated that a locking groove or notch may be provided instead of a locking projection to engage the first end 132 of the locking lever 130. The locking lever 130 has a second end 134 that is engageable by the sleeve 128 to move the first end 132 into and out of locking engagement with the projection 138. An overcenter spring 136 is provided between the locking lever 130 and the sleeve 128 to bias the locking lever 130 into both the locking position and the unlocked position. The connector may be disconnected from the components 40, 42 by moving the sleeve 128 toward the component 42. Movement of the sleeve 128 toward the second end 134 of the lever 130 will cause the sleeve to engage the second end 134 of the lever 130 and pivot the first end 132 of the lever 130 out of engagement with the projection 138. Movement of the sleeve 128 in the opposite direction, i.e. toward the first end 132 of the lever 130, will cause the sleeve 128 to engage the first end 132 of the lever 130 to pivot the first end 132 into engagement with the projection 138 and form a connection.

FIG. 13b illustrates a variation of the sleeve 128. The sleeve 128 includes a notch 129. The sleeve 128 can be squeezed to increase its diameter and allow the sleeve 128 to be moved from the connection position to the disconnection position, and vice versa. When the squeeze on the sleeve is released, the sleeve returns to its original diameter to engage the lever. The notched sleeve eliminates the need for the overcenter spring for biasing the lever.

2.12 Thirteenth Embodiment

Referring to FIG. 14, a connector includes levers 142 pivotally attached to component 40. The levers 142 are biased by springs, or spring-like elements, 144 into a connection position. An end 143 of each lever 142 engages a circumferential projection 150 on the end of component 42. An end of the component 40 includes a projecting rim 146 configured to engage a circumferential groove 148 in component 42. A sealing ring 140 may be provided between the components 40, 42 to make the connection substantially leakproof. It should also be appreciated that magnets may be provided to the ends of the components to aid in positioning and establishing an initial connection between the components 40, 42.

To disconnect the components 40, 42, the levers 142 are depressed against the bias of springs 144 to release the ends 143 of the levers 142 from engagement with the projections 150. It should be appreciated that instead of spring biased levers, the connector may include an expandable cuff that expands when squeezed at one end and contracts when released. The expandable cuff may be squeezed and moved over the projecting rim 146 and circumferential groove 148 and then released to contract around the rim 146 and groove 148 to maintain the connection of the components 40, 42. It should also be appreciated that an expandable cuff may be provided over the levers 142 to cause the ends 143 of the levers 142 to move into and out of engagement with the circumferential projection 150.

2.13 Fourteenth Embodiment

Figure 15A:
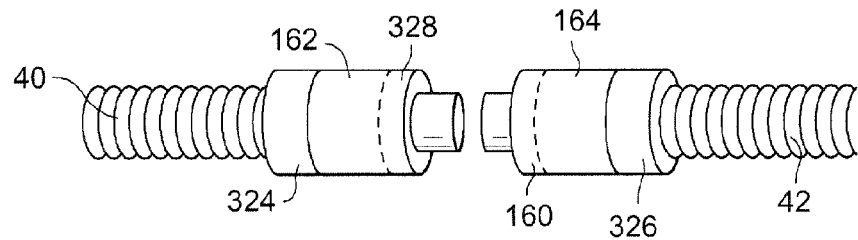
FIGS. 15a-15e illustrate a connector according to an embodiment of the invention.
Figure 15B:
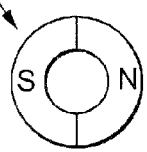
Figure 15C:
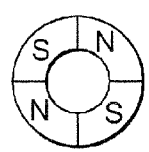
Figure 15D:
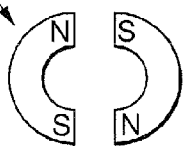
Figure 15E:
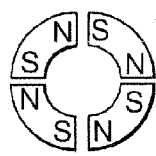

As shown in FIG. 15a, a connector according to another embodiment includes a swivel 154, 156 provided at the end of each component 40, 42, respectively. The swivels 154, 156 include magnetic components that generate an alternating magnetic field. One sample embodiment of this is to use multipole magnets 158, 160 as shown in FIGS. 15b and 15c. The use of this alternating magnetic field on the surface of the connection normal to the axis allows the use of stronger magnets that provide a large axial retention force. However, the connection between the multipole magnets can be easily released, for example by repulsion, by twisting the magnets relative to each other. The magnets may have one or more sets of poles, i.e., 2 or 4 poles, as shown in FIGS. 15b and 15c, or any other number of poles, such as 6, 8, etc. The multipole magnet may be a continuous element having a plurality of magnetic regions, or may include a plurality of discrete magnetic elements, for example a plurality of arc segments or other shaped magnets as shown in FIGS. 15d and 15e. It should be appreciated that a plurality of radially disposed suction cups may be provided instead of the multipole magnets. The suction cups provide a strong axial hold, but are relatively weak in shear so that disconnection is easily achieved by rotation of the components relative to each other.

Referring again to FIG. 15a, the connection between the magnets 158 and 160 is maintained by the swivels 154, 156, which will twist relative to each other before the magnets 158, 160 will twist relative to each other. It should be appreciated that the connection may be maintained by the provision of a single swivel. In order to release the connection, a gripping portion 162, 164 is provided to each swivel 154, 156, respectively. The gripping portions 162, 164 may be gripped by a user to permit the magnets 158, 160 to be rotated relative to each other to release the connection, for example by repulsion. A flexible cover may also be provided over the swivels 154, 156 so that squeezing of the flexible cover permits gripping of the swivels to prevent rotation of the swivels and permit rotation of the magnets 158, 160 relative to each other, and disconnection of the connector.

2.14 Fifteenth Embodiment

Figure 16A:
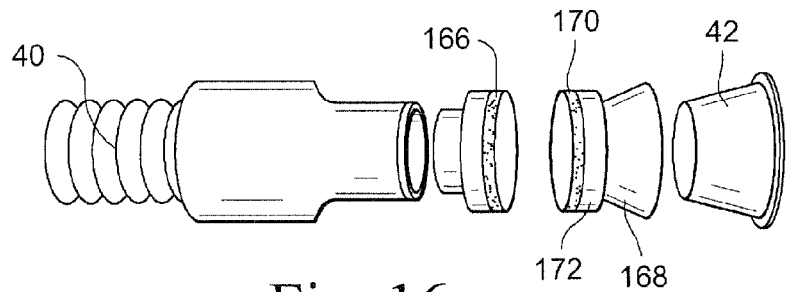
FIGS. 16a and 16b illustrate a connector according to an embodiment of the invention.
Figure 16B:
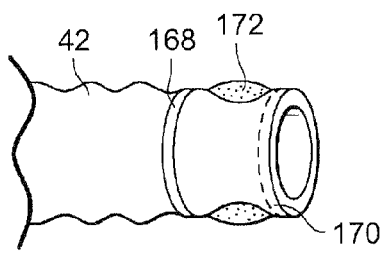

According to another embodiment shown in FIG. 16a, a connector includes a first multipole magnet 166 at an end of component 40 and a swivel 168 and second multipole magnet 170 at an end of component 42. The provision of a single swivel is effective to prevent accidental disconnection of the multipole magnets 166, 170. The magnets may be disconnected by gripping the end of component 40 and a gripping portion 172 of the swivel 168 and twisting the multipole magnets 166, 170 relative to each other. The multipole magnets 166, 170 may have one or more sets of poles, e.g. as shown in FIGS. 15b and 15c. As shown in FIG. 16b, the gripping portion 172a may include overmolded grips. The gripping portion may be manufactured as an adaptor to fit male and female ISO 22 mm connections.

2.15 Sixteenth Embodiment

Figure 17:
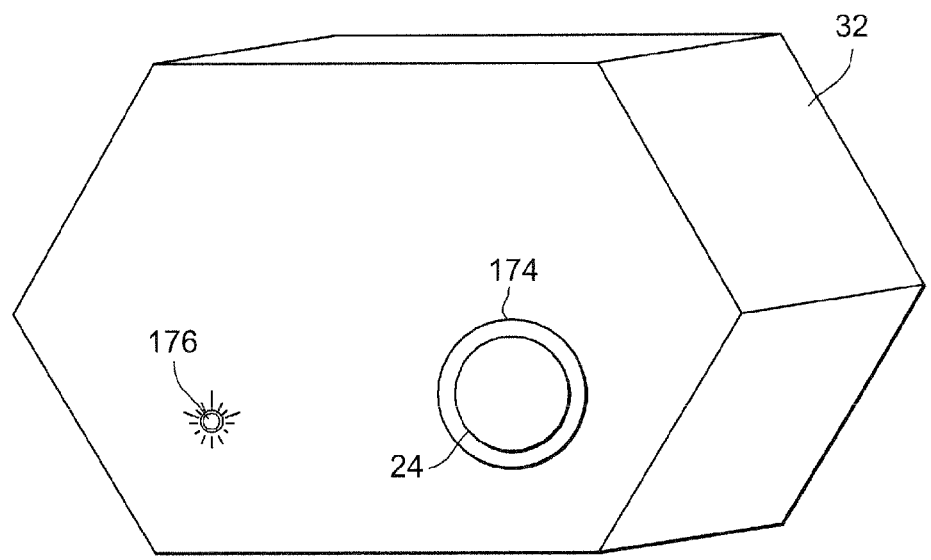
FIG. 17 illustrates a component of a breathing apparatus according to an embodiment of the invention.

Referring to FIG. 17, the outlet 24 of the flow generator 15 may be provided with a magnetic or ferromagnetic connector according to an embodiment of the invention. A switch 174 that detects a change in magnetic field may be provided at the outlet 24 so that upon connection of, for example, the air delivery conduit 16 to the outlet 24, the switch 174 turns on a light 176 to indicate that the connection has been established. The switch 174 may be, for example, a reed switch. The light 176 may also illuminate when the magnet(s) at the end of the conduit 16 is near the magnet(s) of the outlet 24, and then change color when the connection between the conduit 16 and the outlet 24 is established. The light 176 may also fade out after a predetermined time after establishment of the connection. It should be appreciated that more than one light may be provided. For example, a first light of a first color may be illuminated when the end of the delivery conduit 16 is near the outlet 24 of the flow generator 4, and a second light of a second color may be illuminated upon establishment of the connection. The first light may be turned off upon illumination of the second light. The lights may also be used to indicate when the system has been connected incorrectly. The magnetically activated switch may also be used to detect what device has been connected, depending on either different magnetic field shapes, or magnetic strength generated from the air delivery conduit.

2.16 Seventeenth Embodiment

Figure 18A:
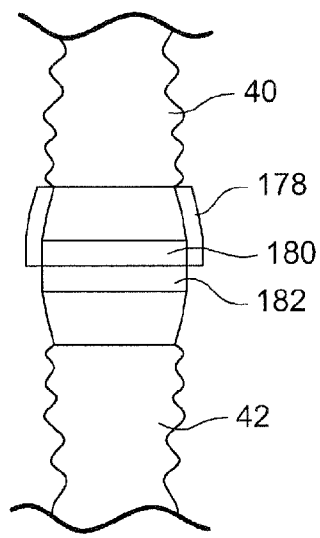
FIGS. 18a and 18b illustrate a connector according to an embodiment of the invention.
Figure 18B:
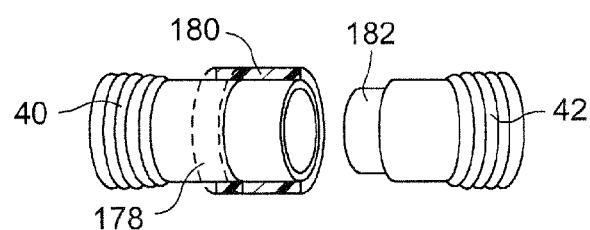

Certain users of the breathing apparatus 1 may have pacemakers to regulate their heart beats. In order to protect the pacemaker from the magnetic field(s) of the connector(s), as shown in FIGS. 18a and 18b, the connector(s) may include magnetic shielding 178. A magnet 180 is provided at one end of component 40 and is shielded by the magnetic shielding 178. To further reduce the potential of the magnetic connector affecting the patient's pacemaker, a ferromagnetic metal 182 is provided at the end of component 42, instead of a magnet. As shown in FIG. 18b, the magnet 180 may be recessed in the end of component 40 to provide additional shielding.

The magnetic shielding 178 increases the magnetic attraction between the magnet 180 and the ferromagnetic metal 182, and thus increases the retention force of the connector. The magnetic shielding 178 may be provided in the form of a cuff that may be slid away from the connection between the magnet 180 and the ferromagnetic metal 182 to decrease the magnetic attraction and allow easier disconnection of the connector.

2.17 Eighteenth Embodiment

Figure 19A:
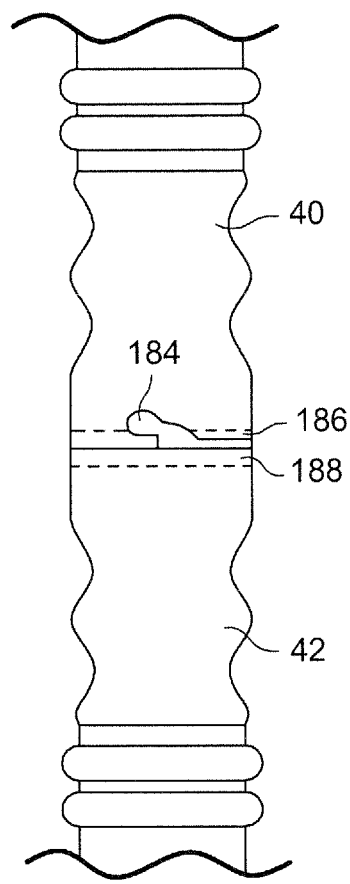
FIGS. 19a-19c illustrate a connector according to an embodiment of the invention.
Figure 19B:
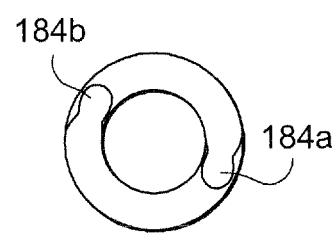

Referring to FIGS. 19a and 19b, a connector includes locking projection 184 extending from component 42 that is received in a correspondingly shaped groove or slot in component 40. Magnets 186, 188 are provided at ends of components 40, 42 to cause an initial contact between the components 40, 42 when the components are placed in close proximity to one another. Once the magnets 186, 188 draw the components into contact, the user rotates the components 40, 42 relative to each other until the locking projection 184 is received in the groove or slot. The insertion of the locking projection 184 into the groove or slot will provide a tactile indication to the user that the connection is complete as the connector will present a smooth, continuous outer circumference. The connector may be disconnected by rotating the components 40, 42 relative to each other in the opposite direction. As shown in FIG. 19b, the connector may include a plurality of locking projections 184a, 184b. It should also be appreciated that the connector need not include the magnets and need not be formed by the locking projection(s) and corresponding groove(s) or slot(s).

2.18 Nineteenth Embodiment

Figure 19C:
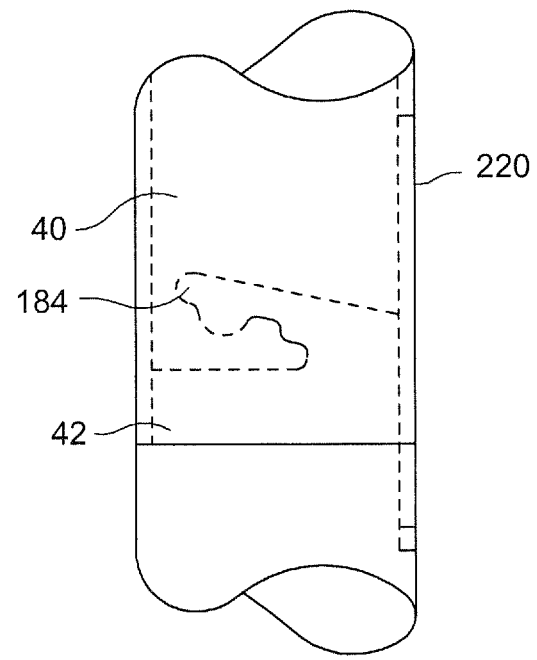

A cover or sleeve 220 may be provided over the components 40, 42 to conceal the connector, as shown FIG. 19c. The cover or sleeve 220 may be configured to assist in generating the seal. For example, the cover or sleeve 220 may be made of a flexible material that is stretched over the components 40, 42 in the area of the connector to maintain or improve the connection. The cover or sleeve 220 also conceals the components of the connector and improves the aesthetic appearance of the components.

2.19 Twentieth Embodiment

Figure 20:
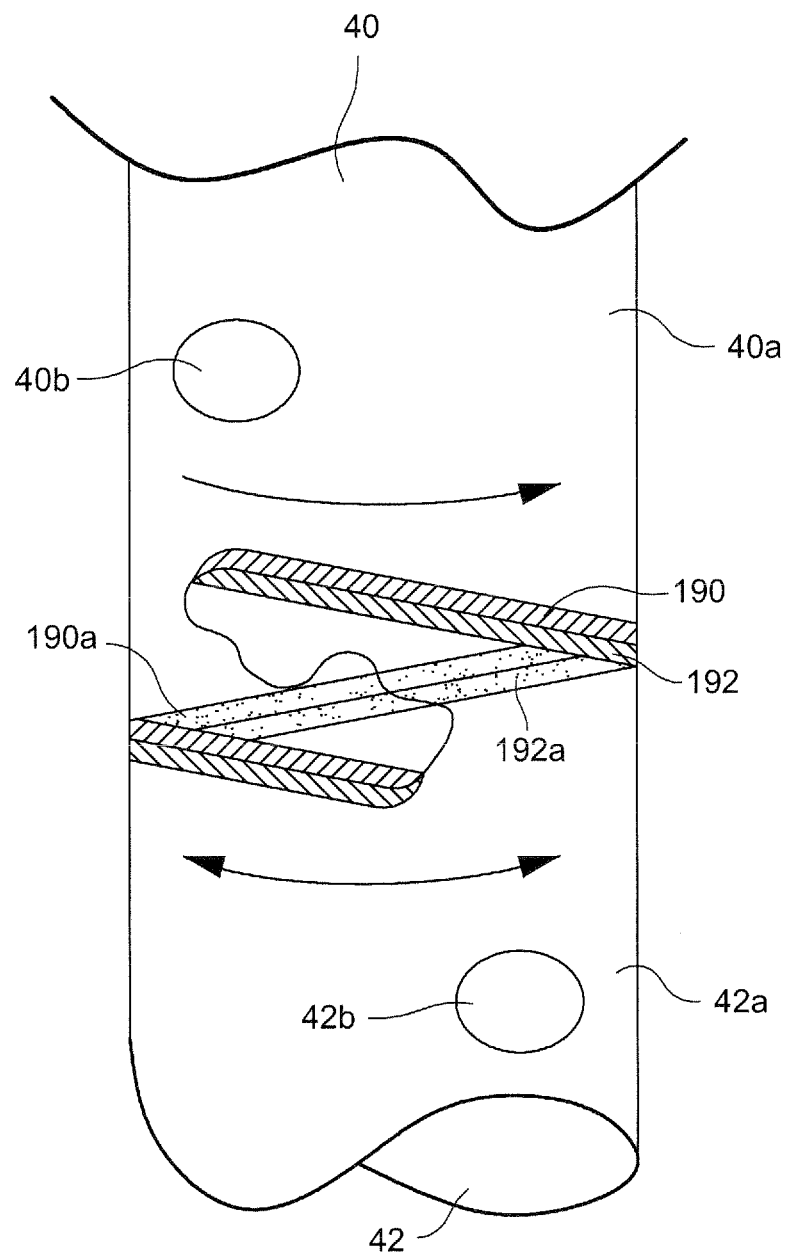
FIG. 20 illustrates a connector according to an embodiment of the invention.

As shown in FIG. 20, ends 40a, 42a of the components 40, 42, respectively, may be formed complementarily to provide a connection. The complementary ends 40a, 42a of the components 40, 42 may be provided with magnets 190, 192, respectively, to cause an initial attraction when the ends 40a, 42a are placed in close proximity, and provide a sealed connection when the ends 40a, 42a are rotated or swiveled relative to one another to form the sealed connection. Each magnet 190, 192 may be provided with a coating 190a, 192a to reduce friction and permit the ends 40a, 42a to be rotated or swiveled relative to each other more easily. The ends 40a, 42a may include a coating or embossing to provide a pleasing tactile feel to the components. Each component may also include a grip indicator 40b, 42b to assist the user in gripping and aligning the ends of the components.

2.20 Twenty-First Embodiment

Figure 21:
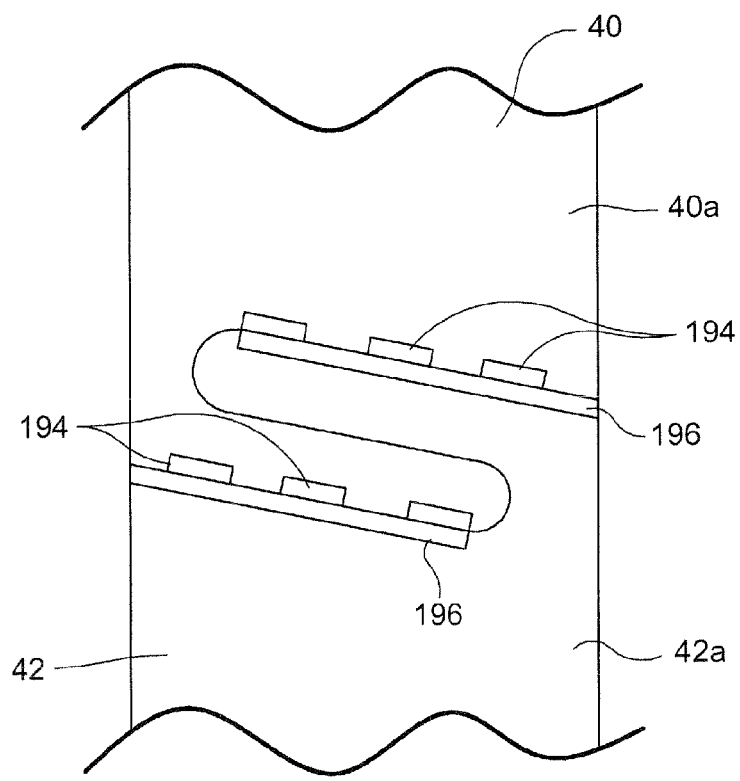
FIG. 21 illustrates a connector according to an embodiment of the invention.

Referring to FIG. 21, the connector may include a magnet or series of magnets 194 at the complementary end 40a of component 40 and a magnetically attractive material 196 at the complementary end 42a of component 42. The magnets 194 and magnetically attractive material 196 assist in the initial attraction of the ends 40a, 42a and form the sealed connection when the components are rotated or swiveled relative to each other into the connected position. The complementary ends 40a, 42a may also include screw threads to prevent disconnection.

2.21 Twenty-Second Embodiment

Figure 22:
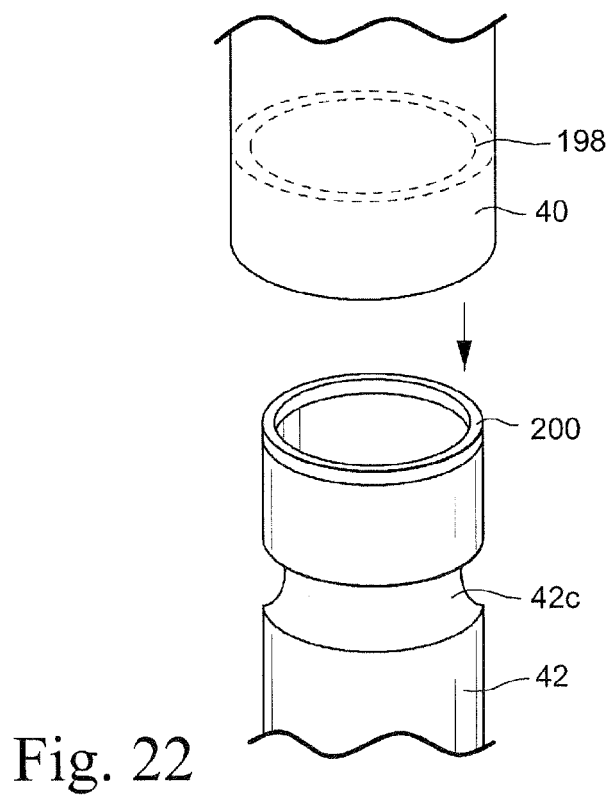
FIG. 22 illustrates a connector according to an embodiment of the invention.
Figure 27A:
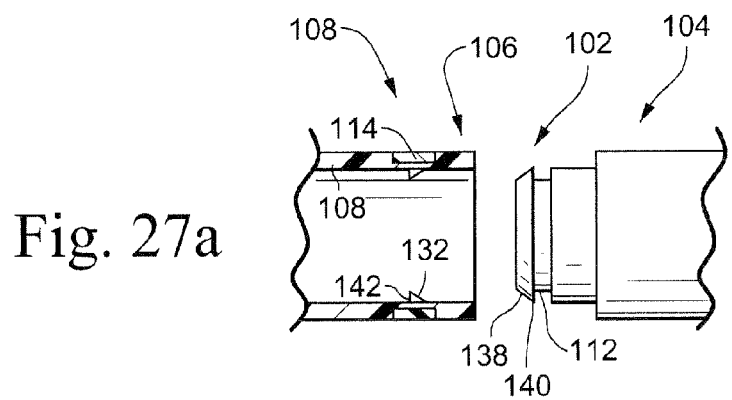
Figure 27B:
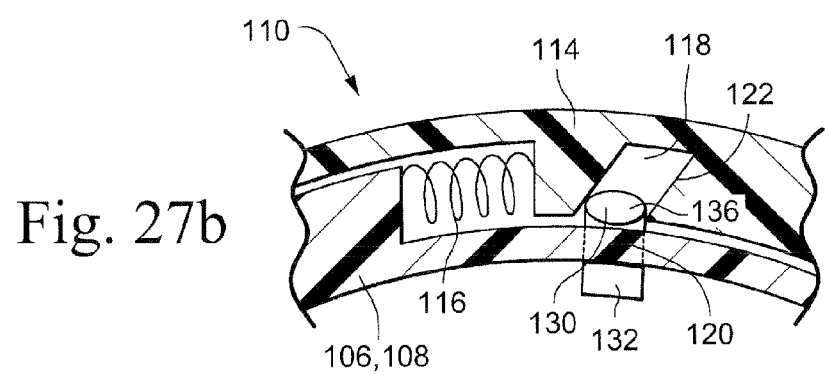
Figure 28A:
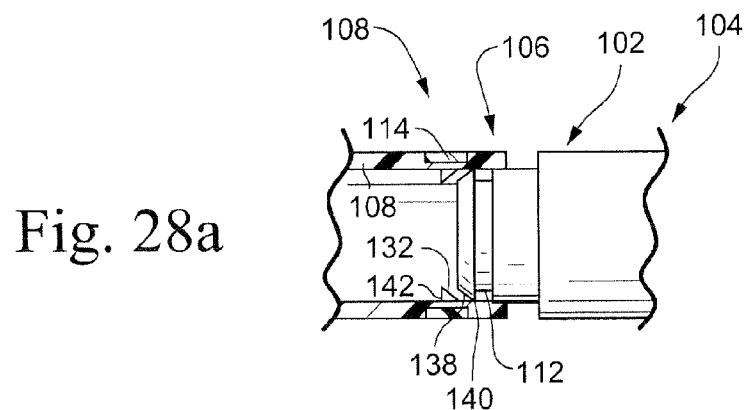
Figure 28B:
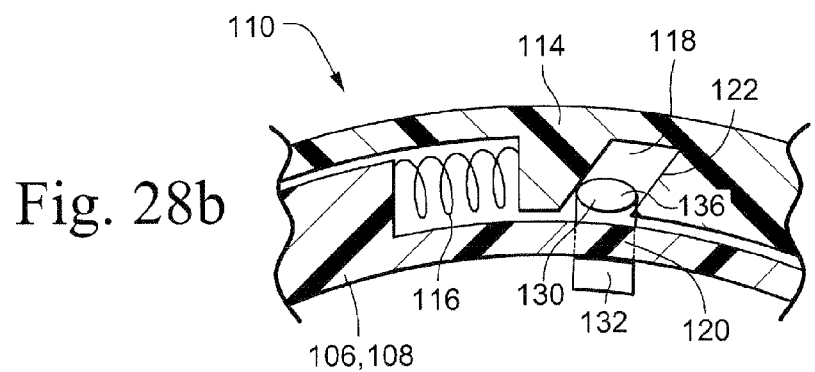
Figure 29A:
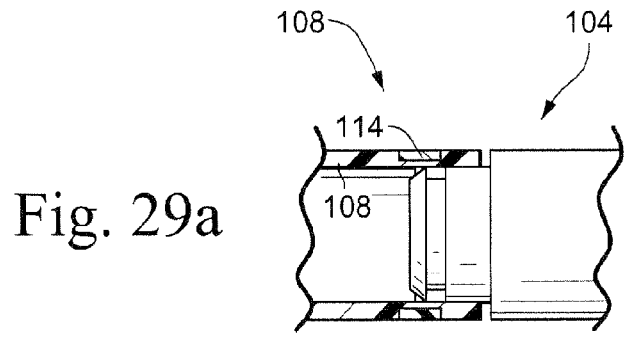
Figure 29B:
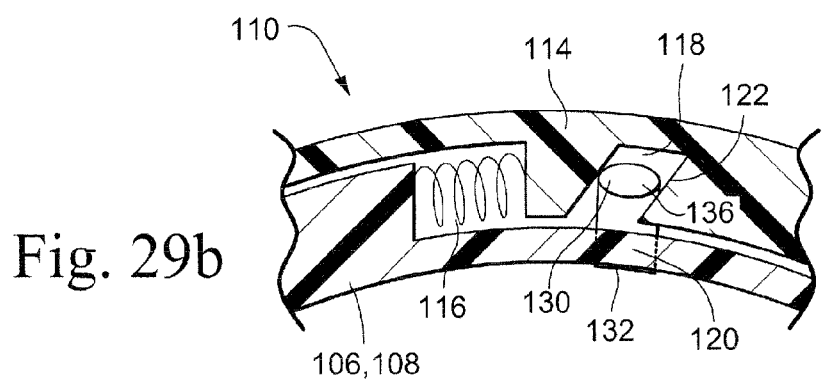
Figure 30A:
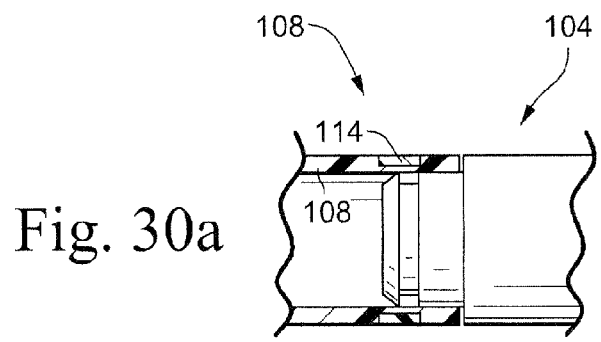
Figure 30B:
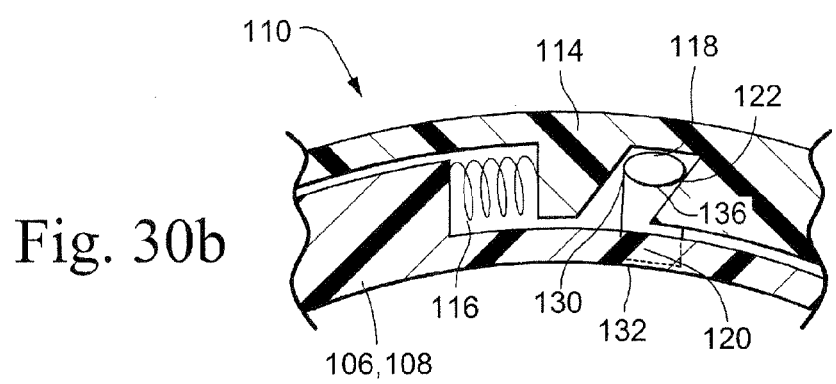
Figure 31A:
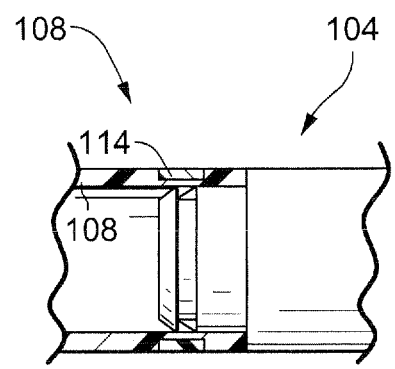
Figure 31B:
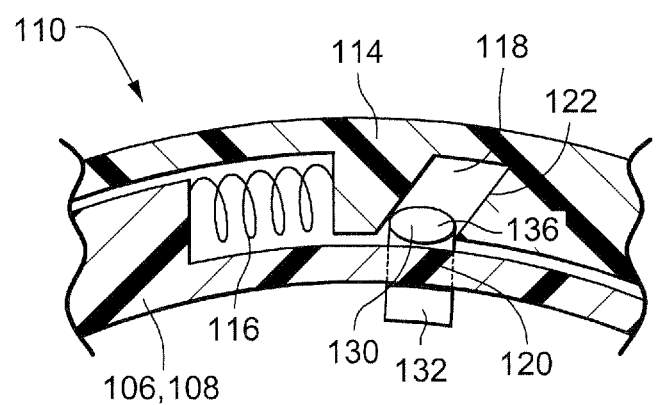

Referring to FIG. 22, a connector may include a flexible ring 198 in component 40 that is received in a groove 42c in component 42. The flexible ring 198 is elastically deformed when component 42 is inserted in component 40, or component 40 is inserted over component 42, and returns to its non-deformed state in the groove 42c. The flexible ring 198 maintains the connection between the components 40, 42 until a release force is applied to the components 40, 42 to elastically deform the ring 198 and remove it from the groove 42c. A gasket 200 may be provided in component 42 to seal the connection between the components 40, 42. It should be appreciated that the gasket may be provided to component 40, or a gasket may be provided to component 40 in addition to the gasket provided to component 42.

2.22 Twenty-Third Embodiment

As shown in FIGS. 23a-23c, a connector may include a soft, flexible ring-shaped flap seal 202. The seal 202 may be formed, for example, of rubber. The seal 202 is provided at the end of component 42 and when a flow of breathable gas is not present, the seal 202 is in the condition shown in FIG. 23a and does not contact the component 40. The component 42 may be inserted into component 40 with minimal force. The components 40, 42 may also be separated or pulled apart with minimal force.

When a flow of breathable gas is present through the components 40, 42, the seal 202 expands as shown in FIGS. 23b and 23c so that the outer circumferential surface of the seal 202 contacts the inner circumferential surface of component 40 to formed a sealed connection. The contact between the seal 202 and the component 40 creates friction that prevents the components 40, 42 from moving axially relative to each other and from separating by application of minimal force. The seal 202 may also be formed as a pneumatic bladder.

2.23 Twenty-Fourth Embodiment

Referring to FIGS. 24-33, a connector for a tube-to-tube connection is illustrated. One end 102 of a first tube 104 is designed for insertion into one end 106 of a second tube 108. The end 106 of the second tube 108 includes a releasable lock 110 and the end 102 of the first tube 104 includes a cooperating circumferential recess/aperture 112. The releasable lock 10 includes a third tube 114 that surrounds at least a portion of the end 106 of the second tube 108. The third tube 114 is rotatable around the second tube 108, but is biased by a spring 116 towards a first position.

Figure 32A:
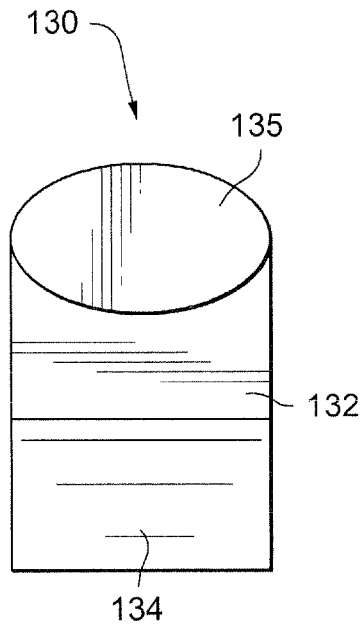
FIGS. 32a-32c schematically illustrate the pin of the connector arrangement of FIG. 24.
Figure 32B:
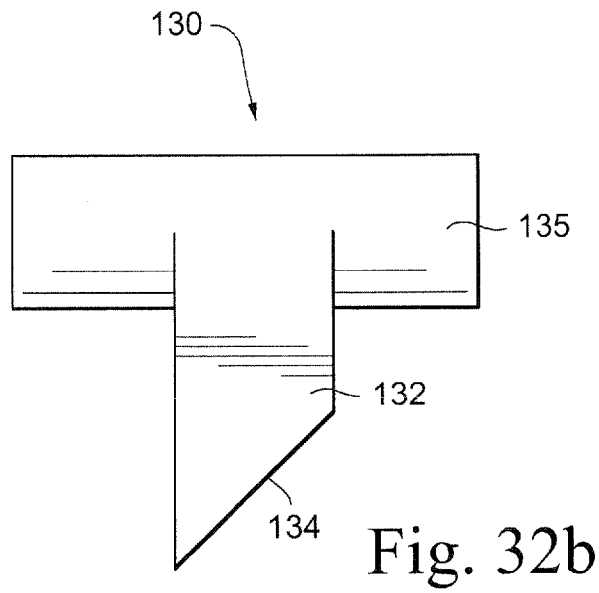
Figure 32C:
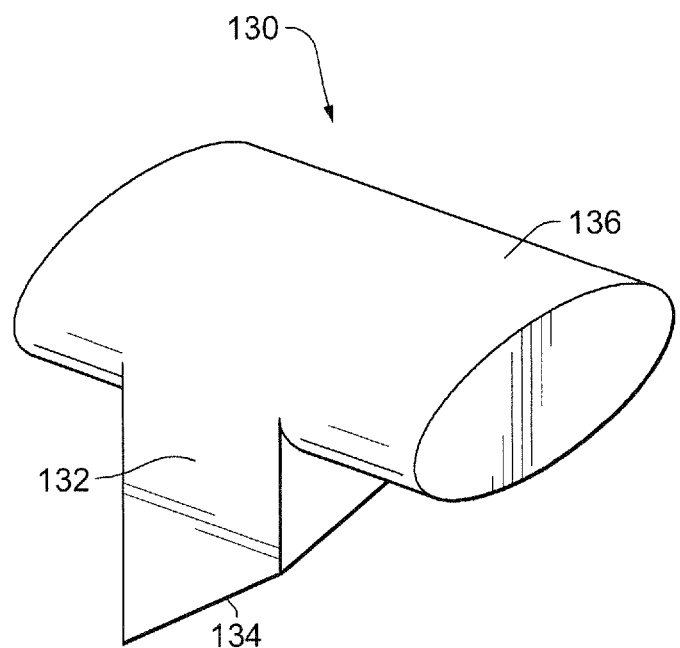
Figure 33:
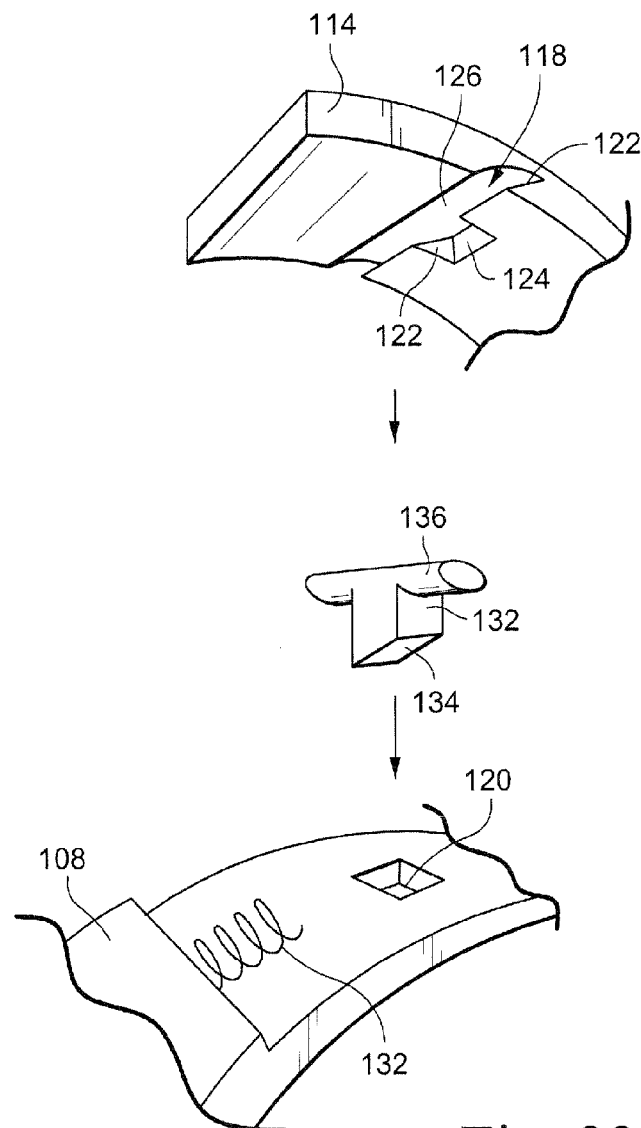

The third tube 114 includes a transverse T-shaped recess 118 (FIG. 33) which is superposed above an aperture 120 in the second tube 108. The aperture 120 is in turn superposed above the circumferential recess 112 around the outside of the first tube 104. The T-shaped recess 118 of the third tube 114 includes two sloping floor surfaces 122 spaced apart by a channel 124 and a sloping ceiling surface 126. A T-shaped pin 130 is provided in the T-shaped recess 118 and is depicted in FIGS. 32a-32c. Although two pins 130 are shown, for example in FIG. 27a, it should be appreciated that the connector may be provided with a single pin, or with more than two pins.

The pin 130 has a stem portion 132 having a sloping surface 134 and a sliding portion 136, which as shown has an elliptical cross-section. It should be appreciated that the sliding portion may have a different cross section such as, for example, a parallelogram or a circle.

The sliding portion 136 of the T-shaped pin 130 is configured to slide up and down the T-shaped recess 118 and the stem 132 of the pin 130 is configured to slide in and out of the channel 124.

The end 102 of the first tube 104 is inserted into the end 106 of the second tube 108. A leading edge 138 of the first tube 104 is sloped or chamfered so that when it contacts the sloping surface 134 of the stem portion 132 of the T-shaped pin 130, the T-shaped pin 130 is urged radially outwards. The sliding portion 136 acts on the sloping ceiling surface 126 of the T-shaped recess 118 to rotate the third tube 114 counterclockwise (in the drawing figures) with respect to the first tube 104 against the bias of the spring 116.

As the T-shaped pin 130 slides radially outward the T-shaped recess 118 the stem 132 of the pin 130 slides into the channel 124 of the recess 118.

Immediately after an outer tip 140 of the sloped leading edge 138 of the first tube 104 passes a trailing side 142 of the stem 132 of the pin 130, the spring 116 urges the pin 130 radially inwardly into locking engagement with the circumferential recess 112 of the first tube 104. In this configuration (FIGS. 31a and 31b) the first tube 104 cannot be removed from the second tube 108.

In order to remove the first tube 104 from the second tube 108, the third tube 114 is rotated counter-clockwise with respect to the second tube 108 to slide the pin 130 out of the circumferential recess 112. When the third tube 114 is released, the pin 130 is once again biased radially inwardly to a position where it will engage the leading edge 138 of the first tube 104 when it is next inserted.

Figure 34:
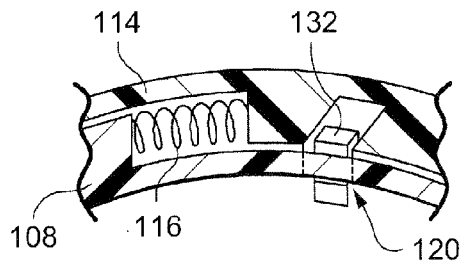
FIGS. 34 and 35 illustrate the operation of the connector arrangement of FIG. 24 from the resting, locked position to the unlocked position.
Figure 35:
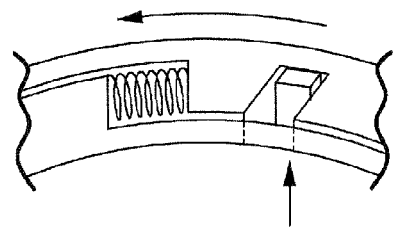

As shown in FIG. 24, the third tube 114 may have gripping features 151 formed in the outer periphery to improve the user's grip on the third tube and permit easier turning of the third tube 114 against the bias of the spring 116. Referring to FIG. 34, in the "resting" position, the stem 132 of the pin 130 extends through the aperture 120 in the second tube 108. When the third tube 114 is rotated relative to the second tube 108 against the bias of the spring 116 (e.g. by the engagement of the leading edge 138 of the first tube 104 with the sloping surface 134 of the pin 130), the stem 132 is confined by the aperture 120 to move radially until it is fully retracted from the interior of the second tube 108 (FIG. 26b). Once the leading edge 138 of the first tube 104 passes the trailing side 142 of the stem 132 of the pin 130, the spring 116 biases the third tube 114 back to the rest position (FIGS. 25b and 34) and the stem 132 moves radially back to engage the circumferential recess 112 in the first tube 104 to connect the first and second tubes.

The third tube 114 acts as a one-way switch, or control, as it is only rotatable by the patient only to unlock the connection between the first and second tubes. The bias of the spring 116 allows the third tube 114 to rotate back to its original position when no turning force is applied to the third tube 114.

2.24 Twenty-Fifth Embodiment

Referring to FIGS. 36-41, a connector arrangement for connecting components or tubes 202, 204 include projections, or "buttons," 206 provided on the outer periphery of one tube 202 that are configured to engage apertures 208 in the outer periphery of the other tube 204. Although three buttons and three apertures are shown in the figures, it should be appreciated that any number of buttons and apertures, including a single button and aperture, may be provided.

As shown in FIGS. 39 and 40, each button 206 is supported on the outer periphery of the tube 202 by a spring, or springs, 210. The springs 210 are provided in a recess 212 in the outer periphery of the tube 202 and bias the button 206 so that the upper surface 206a of the button 206 extends above the outer periphery 202a of the tube 202 when the springs 210 are in a relaxed, uncompressed state. Referring to FIG. 40, when the upper surface 206a of the button 206 is pressed in the direction shown by the arrow, the springs 210 compress and the button 206 is displaced into the recess 212. The button 206 may be depressed until the upper surface 206a is level, or flush, with the outer periphery 202a of the tube 202. The button 206 may also be depressed so that the upper surface 206a is below the level of the outer periphery 202a.

Referring to FIG. 41, the tubes 202, 204 may be connected by inserting the end of the tube 202 including the buttons 206 into the end of the tube 204 including the apertures 208. The end 204b of the tube 204 including the apertures 208 will contact an angled surface 206b of each button 206. As the insertion of tube 202 continues into tube 204, the engagement of the end 204b of the tube 204 with the angled surfaces 206b of the buttons 206 causes depression of the buttons 206. The buttons 206 will be depressed until the upper surfaces 206a contact the inner peripheral surface 204d of the tube 204. The tube 202 is inserted into the tube 204 until a neck 202e of the tube 202 engages the end 204b of the tube 204. At the fully inserted position, the buttons 206 will be biased through the apertures 208 of the tube 204 to complete the connection. If the buttons 206 are not aligned with the apertures 208 in the fully inserted position, the tubes 202, 204 may be rotated relative to each other until the buttons 206 and apertures 208 align, at which point the buttons 206 will be biased by the springs 210 through the apertures 208.

It should be appreciated that the buttons may have a shape other than the generally circular shape shown in FIGS. 36-41. For example, the buttons may have a polygonal or oval shape. The shape of the apertures would correspond to the shape of the buttons. The use of differently shaped buttons and apertures would permit the connection of the tubes to be controlled. For example, the inlet conduit from the flow generator to the humidifier chamber may be specifically designated to have triangular buttons and apertures to ensure that only tubes or conduits designated for use as an inlet conduit could be connected. As another example, the buttons and apertures for the patient conduit may have another, different shape from the buttons and apertures of the inlet conduit to ensure that tubes designated for use as a patient conduit are used only for that purpose. Furthermore, it should be appreciated that the shapes of the buttons and apertures provided to tubes may vary within that connector arrangement. For example, one button and aperture pair may be square, whereas another pair is pentagonal or hexagonal. Such an arrangement would ensure the connection of the tubes in only one way, for example if the tubes were required to be connected in a certain manner to cause, for example, completion of a circuit, for example the connection of a sensor within one of the tubes to a wire or wires carrying information to and/or from the sensor.

Connector with Switch

Figure 42:
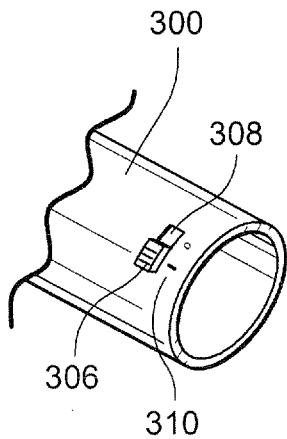
FIG. 42 is a perspective view of a sample embodiment of a connector arrangement including a switch according to the invention.
Figure 43:
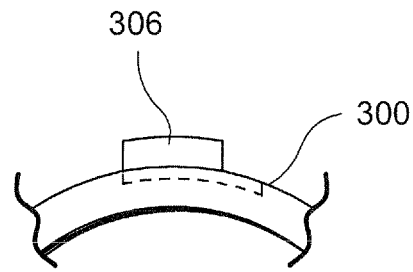
FIG. 43 is an end view of the connector arrangement of FIG. 42.
Figure 44:
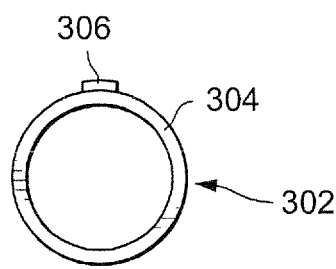
FIG. 44 is a perspective view of the switch of the connector arrangement of FIG. 42.

Referring to FIGS. 42-46, a switch is provided to indicate a connection state of a connector arrangement. As shown in FIGS. 42-44, the switch 302 is provided in an end of a component or tube 300. The switch 302 includes a ring 304 that is provided in the end of the tube 300. The ring 304 comprises a projection 306 that extends through an aperture 308 in the end of the tube 300. The projection 306 may have a textured, e.g. knurled, surface that facilitates gripping by a user's finger(s). The end of the tube 300 also includes indicia 310 that indicates the position of the projection 306, and thus indicates the connection state of the connector engagement. For example, the indicia "1" may indicate that the connector arrangement is in the on, or locked, configuration. The indicia "0" may indicate that the connector arrangement is in the off, or unlocked, configuration.

Figure 45:
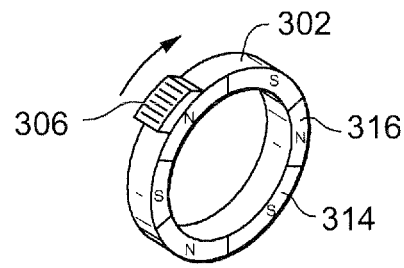
FIG. 45 is a perspective view of a variant of the switch of the connector arrangement of FIG. 42.

The switch of FIGS. 42-46 may be used with the connector arrangements discussed above. For example, as shown in FIG. 45, the ring 304 may include multiple magnetic poles 314, 316, or the ring 304 may be composed of multiple magnets, for example as described with reference to FIGS. 15d and 15e. The connector could be disconnected by rotating the ring 304 in the direction of the arrow by pushing the projection 306. The connection between two magnetic connectors would disengage when the ring 304 is rotated such that identical magnetic poles oppose each other. The repulsive force generated by the identical magnetic poles would cause the connector to unlock or disengage.

Figure 46:
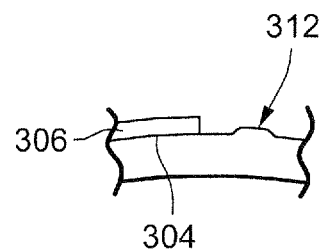
FIG. 46 is an end view of a variant of the switch of the connector arrangement of FIG. 42.

The switch may also include a smaller projection, or bump 312, as shown in FIG. 46 to prevent the switch from accidentally moving from the engaged to disengaged position and/or prevent unstable transitions between the two states. The bump 312 may be configured to provide resistance to movement (i.e. rotation) of the ring 304 so the projection 306, and hence the ring 304, is not inadvertently, or unintentionally, moved from the engaged to the disengaged position. The bump 312 is configured to engage the edge of the aperture 308 and/or the inner surface of the tube 300 to provide frictional resistance to movement of the ring 304 and projection 306.

It should be appreciated that the magnets disclosed above with respect to the illustrated embodiments may be permanent magnets or electromagnets, or combinations of both. For example, an electromagnet(s) may be used so that when the flow generator is turned on, the electromagnets are energized to form and maintain the connection. If there is a fault in the flow generator, the electromagnet(s) is turned off and the connector is disconnected. This would allow the elimination of an automatic shut-off valve. As another example, a fault in the flow generator could cause a reversal in the electromagnet(s) to cause the air delivery conduit or hose to be repelled away from the patient interface (e.g. mask). A combination of a permanent magnet(s) and an electromagnet(s) may be provided to produce the same effect. A strong electromagnet may form a connector for two components, but upon detection of a fault, the electromagnet is switched off and a weaker permanent magnet(s) repels the components apart. The use of electromagnets would also prevent components from sticking together when in storage, as may occur if permanent magnets are used.

A circuit may be provided to induce a signal to the flow generator when the magnets are brought into connection. The magnets may be matched to specific components of the system (e.g. to a specific type of mask) so that the characteristics of the signal indicate the component that is connected.

It should also be appreciated that a deformable cuff, cover or sleeve, for example the one shown in FIG. 19c, may be provided with a wedge or lever on its inner surface to release or assist in releasing the connection. Squeezing the cuff, cover or sleeve would cause the wedge or lever to engage with the connector to force the magnets apart, either partially or entirely. A cuff may be configured as a gel cuff which can be deformed by squeezing in and out of a position where the components interlock. A pneumatic bladder may also be used instead of a gel cuff.

The connector may also be formed such that it can be connected or disconnected by changing the properties of the material. For example, the connector could be formed of wax which may be melted to allow the connector to be disconnected.

It should also be appreciated that the polarity of the magnets may be configured to ensure that components of the system are connected in a correct order. The strengths of the magnets may also be configured to control the strength of the connections. The components may be scaled in a hierarchy of importance and the release forces adopted with respect to system integrity. For example it would be advantageous from a safety perspective for the release force of a connection between the humidifier and the gas conduit interconnecting with patient interface to have a release force that is lower than the release force applicable to the connections for the gas conduit inter connecting the humidifier to an in-line filter and the force required to move the flow generator. This configuration would operate such that if a pull force was applied to the gas conduit which interconnects the humidifier to the patient interface the connection between the gas conduit and the humidifier would surrender to the pull force and thereby prevent a humidifier from being pulled towards the user. The force required to move the humidifier would be greater than the release force to further reduce the opportunity for the humidifier to move. Furthermore if the circuit includes an in-line filter intended to protect the flow generator from contamination sourced from the user interface end of the breathing circuit then the placement of the connection having the lowest release force would be at a location that is closer to the user interface than the location of the connection or connections linking the air delivery pathway between the in-line filter and the flow generator. By operation of the release device, should the relevant connection be subjected to a magnitude of pull force that is at least as great as the relevant release force then the system contamination prevention system remains intact.

When determining the maximum release force for the connection or connections between the flow generator and the in-line filter, a decision may be made to set it at a level that is equal to or greater than the move force for the flow generator. When making that decision a determination may be made as to the preferable consequence of a pull force. Consideration is given as to whether it is preferable to the system's integrity for the connections between the in-line filter and flow generator to yield to the pull force before the flow generator moves or vice versa. Either configuration may be achieved through adoption of embodiments of the present invention.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A connector for connecting components of a breathing apparatus, the components including at least a flow generator for generating a flow of breathable gas, a patient interface, and a delivery conduit for delivering the breathable gas from the flow generator to the patient interface, the connector comprising:

a male connector extending from an end of a first component, the male connector comprising a recess; and a female connector extending from an end of a second component, the female connector comprising a lever pivotably connected to female connector, wherein the male connector is insertable into the female connector so that at least a portion of an outer wall of the female connector encloses an inserted end of the male connector and so that the lever engages the recess and connects the first and second components, wherein the lever is separate from the outer wall of the female connector.

2. A connector according to claim 1, wherein the lever comprises a first projection that engages the recess of the male connector.

3. A connector according to claim 2, wherein the female connector comprises an inner casing and an outer casing, and the lever is pivotably connected to the inner casing.

4. A connector according to claim 3, further comprising a first spring configured to pivotably bias the lever toward the outer casing.

5. A connector according to claim 4, further comprising a second spring between the inner and outer casing configured to bias a projection of the outer casing into engagement with a second projection of the lever.

6. A connector according to claim 5, wherein the first spring and the second spring are integral.

7. A connector according to claim 5, wherein disengagement of the projection of the outer casing from the second projection of the lever disengages the first projection of the lever from the recess of the male connector.

8. A connector according to claim 7, wherein movement of the outer casing relative to the inner casing in a first direction disengages the projection of the outer casing from the second projection.

9. A connector according to claim 8, wherein movement of the male connector in a second direction opposite the first direction disconnects the male connector from the female connector.

10. A connector according to claim 4, wherein the engagement of the projection of the outer casing with the second projection biases the lever toward the inner casing.

11. A combination, comprising:
a connector according to claim 1; and
a switch comprising a ring provided in an end of the first or the second component, the ring comprising a projection extending through an aperture in the end of the first or the second component, wherein the projection is movable between a first position that indicates a connected state of the connector, and a second position that indicates an unconnected state of the connector.

12. A combination according to claim 11, wherein the first or the second component has indicia indicating the first and second positions of the switch.

13. A positive airway pressure device, comprising:
a flow generator to generate a flow of gas pressurized in a range of about 4-30 cm of $H_2O$;
a patient interface;
an air delivery conduit between the flow generator and the patient interface; and
a connector according to claim 1.

14. A positive airway pressure device according to claim 13, further comprising a switch, the switch comprising a ring provided in an end of the first or the second component, the ring comprising a projection extending through an aperture in the end of the first or the second component, wherein the projection is movable between a first position that indicates a connected state of the connector, and a second position that indicates an unconnected state of the connector.

15. A positive airway pressure device, comprising:
a flow generator to generate a flow of gas pressurized in a range of about 4-30 cm of $H_2O$;
a patient interface;
an air delivery conduit between the flow generator and the patient interface; and
a combination according to claim 11.

16. A patient interface, comprising:
a frame;
a cushion provided to the frame; and
a connector according to claim 1.

17. A patient interface according to claim 16, further comprising a switch comprising a ring provided in an end of the first or the second component, the ring comprising a projection extending through an aperture in the end of the first or the second component, wherein the projection is movable between a first position that indicates a connected state of the connector, and a second position that indicates an unconnected state of the connector.

18. A patient interface, comprising:
a frame;
a cushion provided to the frame; and
a combination according to claim 11.

19. A switch for indicating a connection state of a connector for connecting components of a breathing apparatus, the components including at least a flow generator for generating a flow of breathable gas, a patient interface, and a delivery conduit for delivering the breathable gas from the flow generator to the patient interface, the switch comprising:
a ring provided in an end of a first or a second component, the ring comprising a projection extending through an aperture in an end of the first or the second component, wherein the projection is movable between a first position that indicates a connected state of the connector, and a second position that indicates an unconnected state of the connector.

20. A switch according to claim 19, wherein the ring comprises a plurality of magnetic poles.

21. A switch according to claim 19, wherein the ring comprises a second projection configured to frictionally engage an inner surface of the first or second component to prevent unintended movement of the ring from the first position to the second position.

22. A connection system for connecting a first air delivery conduit to a port or a second air delivery conduit, the connection system comprising:
a male connector adapted to be connected to a first component selected from the first air delivery conduit, the port or the second air delivery conduit, the male connector having a recess;
a female connector adapted to be connected to a second component selected from the first air delivery conduit, the port or the second air delivery conduit, the female connector having an outer wall, at least a portion of which is axially retractable, and an engagement device configured to engage the recess,
wherein the male connector is configured to be insertable into the female connector to form a connection between the first component and the second component, and
wherein the engagement device is biased toward a central portion of the female connector when the outer wall of the female connector is in an extended position and is biased toward an exterior of the female connector when the outer wall of the female connector is in a retracted position.

23. A connection system according to claim 22, wherein the engagement device is configured to be continuously biased toward the exterior of the female connector.

24. A connection system according to claim 23, wherein the female connector has an inner wall, and the engagement device is pivotably secured to the inner wall.

25. A connection system according to claim 24, wherein the outer wall extends beyond the inner wall and encloses the engagement device in the extended position.

26. A connection system according to claim 25, wherein the female connector further comprises a first spring positioned between the inner wall and the engagement device, the first spring biasing the engagement device toward the exterior of the female connector.

27. A connection system according to claim 26, wherein the female connector further comprises a second spring positioned between the inner and outer walls, the second spring biasing the outer wall toward an extended position.

28. A connection system according to claim 27, wherein the outer wall biases the engagement device toward the central portion of the female connector when the outer wall is in contact with the engagement device.

29. A connection system according to claim 28, wherein the outer wall biases the engagement device toward the central portion of the female connector when the outer wall is in the extended position.

30. A connection system according to claim 29, wherein the engagement device comprises a first projection configured to engage the recess.

31. A connection system according to claim 30, wherein the outer wall includes a lip, and the engagement device comprises a second projection configured to engage the lip.

32. A connection system according to claim 31, wherein the first and second springs are integral to each other.

33. A positive airway pressure device, comprising:
   a flow generator to generate a flow of gas pressurized in a range of about 4-30 cm of $H_2O$;
   a patient interface;
   an air delivery conduit between the flow generator and the patient interface; and
   a connection system according to claim 23.

34. A positive airway pressure device according to claim 33, further comprising a switch, the switch comprising a ring provided in an end of the first air delivery conduit, the port or the second air delivery conduit, the ring comprising a projection extending through an aperture in the end of the first air delivery conduit, the port or the second air delivery conduit, wherein the projection is movable between a first position that indicates a connected state of the connection system, and a second position that indicates an unconnected state of the connection system.

35. A connection system for connecting a first air delivery conduit to a port or a second air delivery conduit, the connection system comprising:
   a male connector;
   a female connector having an outer wall, at least a portion of which is axially retractable,
   wherein the male connector is configured to be insertable into the female connector to form a connection,
   wherein the male connector and the female connector are configured so that the male connector is removable from the female connector when the outer wall of the female connector is retracted and so that the male connector is not removable from the female connector when the outer wall is extended, and
   wherein the outer wall of the female connector is configured to automatically retract and extend upon insertion of the male connector into the female connector.

36. A connection system according to claim 35, wherein the female connector comprises an engagement device configured to engage a recess on the male connector, wherein the engagement device is configured to engage the recess when the outer wall is extended and disengage from the recess when the outer wall is retracted.

37. A connection system according to claim 36, wherein the male connector and the female connector are configured so that when initially inserted into the female connector, the male connector forces the engagement device against the outer wall of the female connection.

38. A connection system according to claim 37, wherein the outer wall is configured so that when the male connector forces the engagement device against the outer wall, the outer wall axially retracts.

39. A connection system according to claim 38, wherein the outer wall is configured so that when the engagement device engages the recess, the outer wall extends to its fully extended position.

40. A connection system according to claim 39, wherein, when extended, the outer wall of the female device biases the engagement device toward a central portion of the female connector.

41. A connection system according to claim 40, wherein the female connector includes a spring that biases the engagement device toward the outer wall of the female connector.

42. A connection system according to claim 41, wherein the engagement device comprises a first projection configured to engage the recess.

43. A connection system according to claim 42, wherein the outer wall includes a lip, and the engagement device comprises a second projection configured to engage the lip.

44. A connection system according to claim 43, wherein the first and second springs are integral to each other.

45. A positive airway pressure device, comprising:
   a flow generator to generate a flow of gas pressurized in a range of about 4-30 cm of $H_2O$;
   a patient interface;
   an air delivery conduit between the flow generator and the patient interface; and
   a connection system according to claim 35.

46. A positive airway pressure device according to claim 45, further comprising a switch, the switch comprising a ring provided in an end of the first air delivery conduit, the port or the second air delivery conduit, the ring comprising a projection extending through an aperture in the end of the first air delivery conduit, the port or the second air delivery conduit, wherein the projection is movable between a first position that indicates a connected state of the connection system, and a second position that indicates an unconnected state of the connection system.

47. A connection system for connecting a first air delivery conduit to a port or a second air delivery conduit, the connection system comprising:
   a male connector adapted to be connected to a first component selected from the first air delivery conduit, the port or the second air delivery conduit, the male connector having a recess;
   a female connector adapted to be connected to a second component selected from the first air delivery conduit, the port or the second air delivery conduit, the female connector having an outer wall, at least a portion of which is axially retractable, and an engagement device configured to engage the recess,
   wherein the male connector is configured to be insertable into the female connector to form a connection between the first component and the second component, and
   wherein the female connector comprises a biasing element configured to bias the engagement device toward an exterior of the female connector.

48. A connection system according to claim 47, wherein the female connector has an inner wall, and the engagement device is pivotably secured to the inner wall.

49. A connection system according to claim 48, wherein the outer wall extends beyond the inner wall and encloses the engagement device in the extended position.

50. A connection system according to claim 49, wherein the biasing element comprises a first spring positioned between the inner wall and the engagement device, the first spring biasing the engagement device toward the exterior of the female connector.

51. A connection system according to claim 50, wherein the female connector further comprises a second spring positioned between the inner and outer walls, the second spring biasing the outer wall toward an extended position.

52. A connection system according to claim 51, wherein the outer wall biases the engagement device toward the central portion of the female connector when the outer wall is in contact with the engagement device.

53. A connection system according to claim 52, wherein the outer wall biases the engagement device toward the central portion of the female connector when the outer wall is in the extended position.

54. A connection system according to claim 53, wherein the engagement device comprises a first projection configured to engage the recess.

55. A connection system according to claim 54, wherein the outer wall includes a lip, and the engagement device comprises a second projection configured to engage the lip.

56. A connection system according to claim 55, wherein the first and second springs are integral to each other.

* * * * *